US007998981B2

(12) United States Patent
Ramakrishna et al.

(10) Patent No.: US 7,998,981 B2
(45) Date of Patent: Aug. 16, 2011

(54) AMINOARYL SULPHONAMIDE DERIVATIVES AS FUNCTIONAL 5-HT$_6$ LIGANDS

(75) Inventors: Venkata Satya Nirogi Ramakrishna, Hyderabad (IN); Vikas Shreekrishna Shirsath, Hyderabad (IN); Rama Sastri Kambhampati, Hyderabad (IN); Santosh Vishwakarma, Hyderabad (IN); Nagaraj Vishwottam Kandikere, Hyderabad (IN); Srinivasulu Kota, Hyderabad (IN); Venkateswarlu Jasti, Hyderabad (IN)

(73) Assignee: Suven Life Sciences Limited, Hyderabad (IN)

( * ) Notice: Subject to any disclaimer, the term of this patent is extended or adjusted under 35 U.S.C. 154(b) by 471 days.

(21) Appl. No.: 11/990,383

(22) PCT Filed: Oct. 26, 2005

(86) PCT No.: PCT/IN2005/000345
§ 371 (c)(1),
(2), (4) Date: May 22, 2008

(87) PCT Pub. No.: WO2007/020652
PCT Pub. Date: Feb. 22, 2007

(65) Prior Publication Data
US 2010/0168168 A1    Jul. 1, 2010

(30) Foreign Application Priority Data
Aug. 12, 2005 (IN) .......................... 1127/CHE/2005

(51) Int. Cl.
*A61K 31/55* (2006.01)
*A01N 43/00* (2006.01)
*C07D 401/00* (2006.01)
(52) U.S. Cl. ...................... 514/323; 546/201
(58) Field of Classification Search ................. None
See application file for complete search history.

(56) References Cited

U.S. PATENT DOCUMENTS
6,774,241 B2   8/2004   Clark et al.

FOREIGN PATENT DOCUMENTS

| | | |
|---|---|---|
| WO | WO-9827081 A1 | 6/1998 |
| WO | WO-9902502 A2 | 1/1999 |
| WO | WO-9937623 A2 | 7/1999 |
| WO | WO-9942465 A2 | 8/1999 |
| WO | WO-0132646 A2 | 5/2001 |
| WO | WO-02098878 A1 | 12/2002 |
| WO | WO-03065046 A2 | 8/2003 |
| WO | WO-03066056 A1 | 8/2003 |
| WO | WO-03072548 A1 | 9/2003 |
| WO | WO-2004035047 A1 | 4/2004 |
| WO | WO-2004048328 A2 | 6/2004 |
| WO | WO-2004048330 A1 | 6/2004 |
| WO | WO-2004048331 A1 | 6/2004 |
| WO | WO-2004055026 A1 | 7/2004 |
| WO | WO 2005/025558 | * 3/2005 |

OTHER PUBLICATIONS

Lindner et al. An assessment of the effects of serotonin 6 (5-HT6) receptor antagonists in rodent models of learning. The Journal of Pharmacology and Experimental Therapeutics, 2003, vol. 307, No. 2.*
Diagnostic and Statistical Manual of Mental Disorders, Fourth Ed. Text Revision, Chapter on schizophrenia, pp. 297-299, 308-311, American Psychiatric Assn. Pub, 2000.*
Patel (Journal of Geriatric Psychiatry and Neurology, vol. 8, 81-95, 1995).*
Kar et al., J. Psychiatry Neurosci. vol. 29(6): 427-441, 2004.*
Jacobsen et al. (NeuroTherapeutics, vol. 2: 612-626, Oct. 2005).*
Lemere et al. (Rejuvenational Research, vol. 9(1): 77-84, 2006).*
Monsma, F. J., Jr. et al, "Cloning and Expression of a Novel . . . ", Molecular Pharmacology, 1993, 43, 320-327, Am Society for Pharm and Experimental Therapeutics, USA.
Kohen, R. et al, "Cloning, Characterization, and Chromosomal . . . ", Journal of Neurochemistry, 1996, 66, 47-56, Lippincott-Raven Publishers, USA.
Ruat, M. et al, "A Novel Rat Serotonin (5-HT6) Receptor . . . ", Biochemical Biophysical Research Communications, 1993, 193, 268-276, Academic Press.
Ward, R. P. et al, "Localization of Serotonin Subtype 6 Receptor . . . ", Neuroscience, 1995, 64, 1105-1111, Elsevier Science Ltd, UK.
Reavill, C. et al, "The Therapeutic Potential of 5-HT6 . . . ", Current Opinion in Invesigational Drugs, 2001, 2(1):104-109, PharmaPress Ltd.
Gerard, C. et al, "Immuno-localization of serotonin 5-HT6 receptor-like material . . . ", Brain Research, 1997, 746, 207-219, ,Elsevier Science B.V.
Bentley, J. C. et al, "Investigation of stretching behaviour induced by the selective . . . ", British Journal of Pharmacology, 1999, 126 (7), 1537-1542, Stockton Press.
Dawson, L. A. et al, "In vivo effects of the 5-HT6 antagonist . . . ", British Journal of Pharmacology, 2000, 130 (1), 23-26, Macmillan Publishers Ltd.
Rogers, D. C. et al, "The Selective 5HT6 Receptor Antagonist", Society of Neuroscience, Abstracts, 2000, 26, 680, UK.
Ernst, M. et al, "DOPA Decarboxylase Activity in Attention Deficit . . . ", Journal of Neuroscience, 1998, 18(15), 5901-5907, Society for Neuroscience, USA.
Branchek, T. A. et al, Annual Reviews in Pharmacology and Toxicology, 2000, 40, 319-334, Annual Reviews, USA.

(Continued)

*Primary Examiner* — Brandon Fetterolf
*Assistant Examiner* — Anna Pagonakis
(74) *Attorney, Agent, or Firm* — IpHorgan Ltd.

(57) ABSTRACT

The present invention provides aminoaryl sulphonamide derivatives of formula (I), useful in the treatment of a CNS disorder related to or affected by the 5-HT$_6$ receptor. Pharmacological profiles of these components include high affinity binding with 5-HT$_6$ receptors along with good selectivity towards the receptor. The present invention also includes stereoisomers, the salts, methods of preparation and medicine containing the aminoaryl sulphonamide derivatives.

8 Claims, 1 Drawing Sheet

OTHER PUBLICATIONS

Stean, T. et al, "Anticonvulsant Properties of the Selective 5-HT6 Receptor . . . " British Journal of Pharmacology, 1999, 127 Proc. Supplement-131P.

Routledge, C., "Characterization of SB-271046: A Potent . . . ", British Journal of Pharamacology, 2000, 130, 1606-1612, Macmillan Publishers Ltd.

Roth, B.L. et al., "Binding of Typical and Atypical Agents . . . ", Journ of Pharm and Experimental Therapeutics, 1994, 268, pp. 1403-1410, Am Society for Pharm and Exp. Ther.

Sleight, J. et al., Neurotransmission, 1995, 11, 1-5.

Sleight, J. et al., "Serotonin ID Research Alert", 1997, 2(3), 115-118.

Wooley, M.L. et al., "A Role for 5-HT6 Receptors in Retention of Spatial Learning . . . ", Neuropharmacology, 2001, 41: 210-219, Elsevier Science Ltd.

Principles of Asymmetric synthesis, J. E. Baldwin Ed., Tetrahedron series, 14, 311-316, 2004.

Berge, Stephen et al., "Pharmaceutical Salts", Journal of Pharmaceutical Sciences, 1977, 66, 1-19.

Greene, T.W., "Protective Groups in Organic Synthesis", 1991, John Wiley and Sons.

Kask, A. et al., "Neuropeptide Y Y5 Receptor Antagonist CGP71683A . . . ", European Journal of Pharmacology, 414, 2001, 215-224, Elsevier Science B.V.

Turnbull, A. et. al., "Selective Antagonism of the NPY Y5 Receptor Does Not . . . ", Diabetes, 51, 2002, 2441-2449.

Ennaceur, A. et al, "A New One-trial Test for Neurobiological Studies of Memory . . . ", Behavioural Brain Research, 1988, 31, 47-59, Elsevier Science Publishers.

King, M. V. et. al., "5-HT6 Receptor Antagonists Reverse Delay-dependent . . . ", Neuropharmacology, 2004, 47, 195-204, Elsevier Ltd.

Yamada, N. et al., "Improvement of Scopolamine-induced Memory Impairment . . . ", Pharmacology, Biochem. and Behaviour, 2004, 78, 787-791, Elsevier Inc.

Linder, M. D. et al., "An Assessment of the Effects of Serotonin 6 . . . ", Journal of Pharm and Exp. Ther., 2003, 307 (2), 682-691, Am Soc. for Pharm and Exp. Ther., USA.

Callahan, P. M. et al., "Characterization of the Selective 5-HT6 Receptor . . . ", Abstract, 776.19.2004, Society for Neuroscience, 2004.

Fox, G. B. et al., "Memory Consolidation Induces a Transient and . . . ", Journal of Neurochemistry, 1995, 65, 6, 2796-2799, Lippincott-Raven Publishers, USA.

* cited by examiner

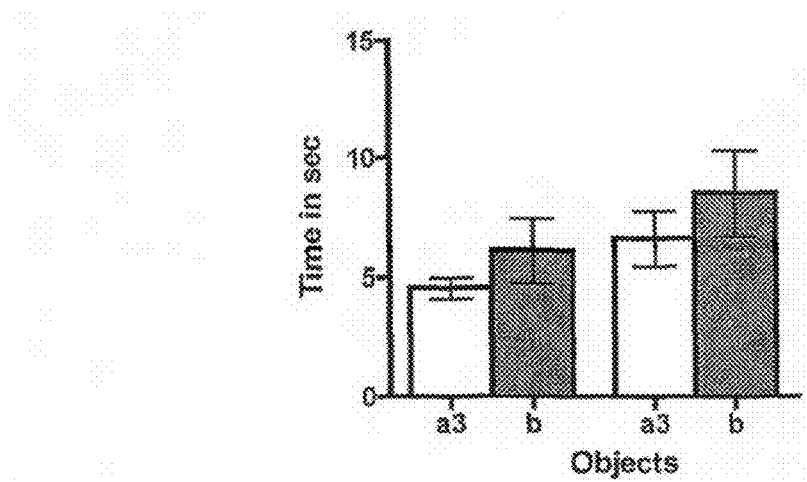
Fig 1. Bar graph demonstrating the effect of treatment of example 6 at 10 mg/Kg orally on the exploration time of animals with novel object, in comparison with the vehicle treated group.
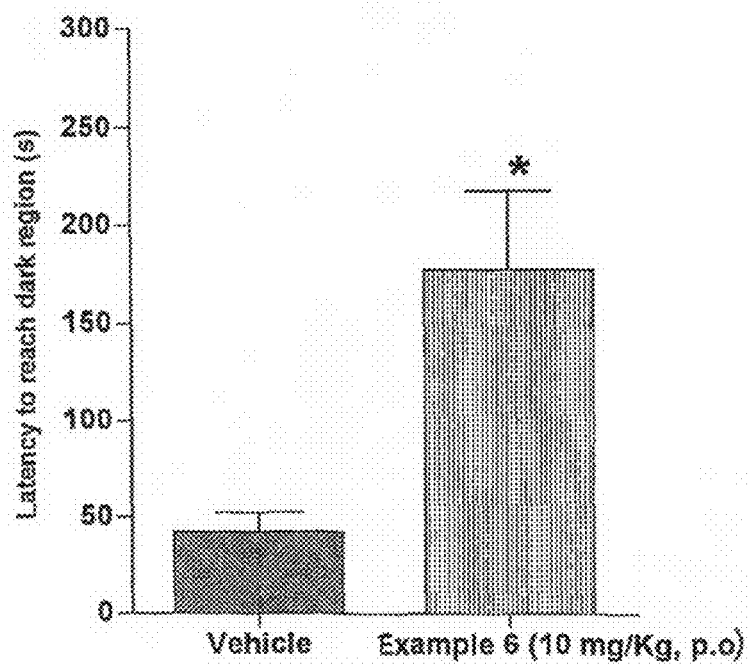
Fig 2. Graph demonstrating the increase in latency to reach the dark zone

AMINOARYL SULPHONAMIDE DERIVATIVES AS FUNCTIONAL 5-HT$_6$ LIGANDS

FIELD OF INVENTION

The present invention relates to certain aminoaryl sulphonamide derivatives, their stereoisomers, their salts, their preparation and medicine containing them.

BACKGROUND OF THE INVENTION

Various central nervous system disorders such as anxiety, depression, motor disorders etc., are believed to involve a disturbance of the neurotransmitter 5-hydroxytryptamine (5-HT) or serotonin. Serotonin is localized in the central and peripheral nervous systems and is known to affect many types of conditions including psychiatric disorders, motor activity, feeding behavior, sexual activity, and neuroendocrine regulation among others. 5-HT receptor subtypes regulate the various effects of serotonin. Known 5-HT receptor family includes the 5-HT$_1$ family (e.g. 5-HT$_{1A}$), the 5-HT$_2$ family (e.g. 5-HT$_{2A}$), 5-HT$_3$, 5-HT$_4$, 5-HT$_5$, 5-HT$_6$ and 5-HT$_7$ subtypes.

The 5-HT$_6$ receptor subtype was first cloned from rat tissue in 1993 (Monsma, F. J.; Shen, Y.; Ward, R. P.; Hamblin, M. W., Molecular Pharmacology, 1993, 43, 320-327) and subsequently from human tissue (Kohen, R.; Metcalf; M. A.; Khan, N.; Druck, T.; Huebner, K.; Sibley, D. R., Journal of Neurochemistry, 1996, 66, 47-56). The receptor is a G-protein coupled receptor (GPCR) positively coupled to adenylate cyclase (Rust, M.; Traiffort, E.; Arrang, J-M.; Tardivel-Lacombe, L.; Diaz, L.; Leurs, R.; Schwartz, J-C., Biochemical Biophysical Research Communications, 1093, 193, 268-276). The receptor is found almost exclusively in the central nervous system (CNS) areas both in rat and in human.

In situ hybridization studies of the 5-HT$_6$ receptor in rat brain using mRNA indicate principal localization in the areas of 5-HT projection including striatum, nucleus accumbens, olfactory tubercle and hippocampal formation (Ward, R. P.; Hamblin, M. W.; Lachowicz, J. E.; Hoffman, B. J.; Sibley, D. R.; Dorsa, D. M., Neuroscience, 1995, 64, 1105-1111). Highest levels of 5-HT$_6$ receptor mRNA has been observed in the olfactory tubercle, the striatum, nucleus accumbens, dentate gyms as well as CA$_1$, CA$_2$ and CA$_3$ regions of the hippocampus. Lower levels of 5-HT$_6$ receptor mRNA were seen in the granular layer of the cerebellum, several diencephalic nuclei, amygdala and in the cortex. Northern blots have revealed that 5-HT$_6$ receptor mRNA appears to be exclusively present in the brain, with little evidence for its presence in peripheral tissues.

The high affinity of a number of antipsychotic agents for the 5-HT$_6$ receptor, in addition to its mRNA localization in striatum, olfactory tubercle and nucleus accumbens suggests that some of the clinical actions of these compounds may be mediated through this receptor. Its ability to bind a wide range of therapeutic compounds used in psychiatry, coupled with its intriguing distribution in the brain has stimulated significant interest in new compounds which are capable of interacting with or affecting the said receptor. At present, there are no known fully selective agonists. Significant efforts are being made to understand the possible role of the 5-HT$_6$ receptor in psychiatry, cognitive dysfunction, motor function and control, memory, mood and the like. To that end, compounds which demonstrate a binding affinity for the 5-HT$_6$ receptor are earnestly sought both as an aid in the study of the 5-HT$_6$ receptor and as potential therapeutic agents in the treatment of central nervous system disorders, for example see C. Reavill and D. C. Rogers, Current Opinion in Investigational Drugs, 2001, 2(1):104-109, Pharma Press Ltd.

There are many potential therapeutic uses for 5-HT$_6$ ligands in humans based on direct effects and on indications from available scientific studies. These studies include the localization of the receptor, the affinity of ligands with known in vivo activity, and various animal studies conducted so far. Preferably, antagonist compounds of 5-h$_6$ receptors are sought after as therapeutic agents. One potential therapeutic use of modulators of 5-HT$_6$ receptor function is in the enhancement of cognition and memory in human diseases such as Alzheimer's. The high levels of receptor found in important structures in the forebrain, including the caudate/putamen, hippocampus, nucleus accumbens, and cortex suggest a role for the receptor in memory and cognition since these areas are known to play a vital role in memory (Gerard, C.; Martres, M. P.; Lefevre, K.; Miguel, M. C.; Verge, D.; Lanfumey, R.; Doucet, E.; Hamon, M.; E I Mestikawy, S., Brain Research, 1997, 746, 207-219). The ability of known 5-HT$_6$ receptor ligands to enhance cholinergic transmission also supported the potential cognition use (Bentey, J. C.; Boursson, A.; Boess, F. G.; Kone, F. C.; Marsden, C. A.; Petit, N.; Sleight, A. J., British Journal of Pharmacology, 1999, 126 (7), 1537-1542).

Studies have found that a known 5-HT$_6$ selective antagonist significantly increased glutamate and aspartate levels in the frontal cortex without elevating levels of noradrenaline, dopamine, or 5-HT. This selective elevation of neurochemicals known to be involved in memory and cognition strongly suggests a role for 5-HT$_6$ ligands in cognition (Dawson, L. A.; Nguyen, H. Q.; Li, P. British Journal of Pharmacology, 2000, 130 (1), 23-26). Animal studies of memory and learning with a known selective 5-HT$_6$ antagonist found some positive effects (Rogers, D. C.; Hatcher, P. D.; Hagan, J. J. Society of Neuroscience, Abstracts, 2000, 26, 680).

A related potential therapeutic use for 5-HT$_6$ ligands is the treatment of attention deficit disorders (ADD, also known as Attention Deficit Hyperactivity Disorder or ADHD) in both children and adults. Because 5-HT$_6$ antagonists appear to enhance the activity of the nigrostriatal dopamine pathway and because ADHD has been linked to abnormalities in the caudate (Ernst, M; Zametkin, A. J.; Matochik, J. H.; ions, P. A.; Cohen, R. M., Journal of Neuroscience, 1998, 18(15), 5901-5907), 5-HT$_6$ antagonists may attenuate attention deficit disorders.

International Patent Publication WO 03/066056 A1 reports that antagonism of 5-HT$_6$ receptor could promote neuronal growth within the central nervous system of a mammal. Another International Patent Publication WO 03/065046 A2 discloses new variant of human 5-HT$_6$ receptor, and proposes that human 5-HT$_6$ receptor is being associated with numerous other disorders.

Early studies examining the affinity of various CNS ligands with known therapeutic utility or a strong structural resemblance to known drugs suggests a role for 5-HT$_6$ ligands in the treatment of schizophrenia and depression. For example, clozapine (an effective clinical antipsychotic) has high affinity for the 5-HT$_6$ receptor subtype. Also, several clinical antidepressants have high affinity for the receptor as well and act as antagonists at this site (Branchek, T. A.; Blackburn, T. P., Annual Reviews in Pharmacology and Toxicology, 2000, 40, 319-334).

Further, recent in vivo studies in rats indicate that 5-HT$_6$ modulators may be useful in the treatment of movement disorders including epilepsy (Stean, T.; Routledge, C.; Upton, N., British Journal of Pharmacology, 1999, 127 Proc. Supplement-131P; and Routledge, C.; Bromidge, S. M.; Moss, S. F.; Price, G. W.; Hirst, W.; Newman, H.; Riley, G.; Gager, T.; Stean, T.; Upton, N.; Clarke, S. E.; Brown, A. M., British Journal of Pharmacology, 2000, 30 (7), 1606-1612).

Taken together, the above studies strongly suggest that compounds which are 5-HT$_6$ receptor modulators, i.e. ligands, may be useful for therapeutic indications including: the treatment of diseases associated with a deficit in memory, cognition, and learning such as Alzheimer's and attention deficit disorder; the treatment of personality disorders such as schizophrenia; the treatment of behavioral disorders, e.g. anxiety, depression and obsessive compulsive disorders; the treatment of motion or motor disorders such as Parkinson's disease and epilepsy; the treatment of diseases associated with neurodegeneration such as stroke or head trauma; or withdrawal from drug addiction including addiction to nicotine, alcohol, and other substances of abuse.

Such compounds are also expected to be of use in the treatment of certain gastrointestinal (GI) disorders such as functional bowel disorder. See for example, B. L. Roth et al., J. Pharmacol. Exp. Ther., 1994, 268, pages 1403-14120, D. R. Sibley et al., Molecular Pharmacology, 1993, 43, 320-327, A. J. Sleight et al., Neurotransmission, 1995, 11, 1-5, and A. J. Sleight et al., Serotonin ID Research Alert, 1997, 2(3), 115-118.

Furthermore, the effect of 5-HT$_6$ antagonist and 5-HT$_6$ antisense oligonucleotides to reduce food intake in rats has been reported thus potentially in treatment of obesity. See for example, Bentley et al., British Journal of Pharmacology, 1999, Suppl., 126, A64: 255; Wooley et al., Neuropharmacology, 2001, 41: 210-129; and WO 02/098878.

International Patent Publications WO 2004/055026 A1, WO 2004/048331 A1, WO 2004/048330 A1 and WO 2004/048328 A2 (all assigned to Suven Life Sciences Limited) describes related prior art. These PCT applications and the references reported therein are all incorporated herein. Further WO 98/27081, WO 99/02502, WO 99/37623, WO 99/42465 and WO01/32646 (all assigned to Glaxo SmithKline Beecham PLC) disclose a series of aryl sulphonamide and sulphoxide compounds as 5-HT$_6$ receptor antagonists and which are claimed to be useful in the treatment of various CNS disorders. While some 5-HT$_6$ modulators have been disclosed, there continues to be a need for compounds that are useful for modulating 5-HT$_6$.

Therefore, it is an object of this invention to provide compounds, which are useful as therapeutic agents in the treatment of a variety of central nervous system disorders related to or affected by the 5-HT$_6$ receptor.

It is another object of this invention to provide therapeutic methods and pharmaceutical compositions useful for the treatment of central nervous system disorders related to or affected by the 5-HT$_6$ receptor.

It is a feature of this invention that the compounds provided may also be used to further study and elucidate the 5-HT$_6$ receptor.

The preferred object of the invention to synthesize a potent selective 5-HT$_6$ receptor antagonist.

SUMMARY OF THE INVENTION

Aminoacyl sulphonamide class of compounds has now been found which demonstrate 5-HT$_6$ receptor affinity, which may be used as effective therapeutic agents for the treatment of central nervous system (CNS) disorders.

(i) The present invention relates to a compound of the Formula (I), along with its stereoisomer or its salt with an inorganic or organic acid.

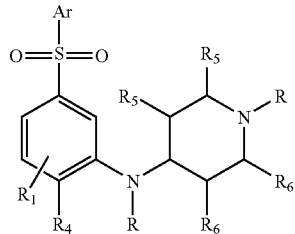

Formula (I)

wherein:
Ar represents any one group selected from phenyl, naphthyl, a monocycle or bicyclic heteroaryl, each of which may be further substituted by one or more independent substituents and those substituents are defined as R$_1$;

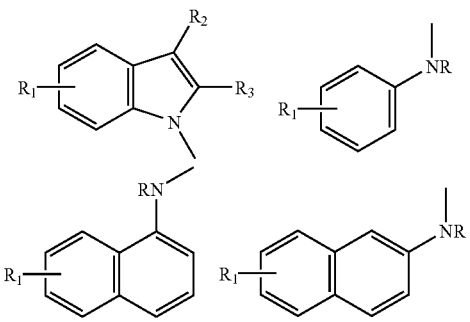

R represents either a hydrogen atom, (C$_1$-C$_3$)alkyl or halo (C$_1$-C$_3$)alkyl group;
R$_1$ and R$_4$ independently represents one or multiple substitutions on the benzene ring, and includes a hydrogen, halogen, cyano, (C$_1$-C$_3$)alkyl, halo(C$_1$-C$_3$)alkyl, (C$_1$-C$_3$)alkoxy, halo(C$_1$-C$_3$)alkoxy, cyclo(C$_3$-C$_6$)alkyl or cyclo(C$_3$-C$_6$)alkoxy;
R$_2$ whenever present, represents hydrogen, halogen, (C$_1$-C$_3$)alkyl, halo(C$_1$-C$_3$)alkyl, (C$_1$-C$_3$)alkoxy or halo(C$_1$-C$_3$)alkoxy;
R$_3$ whenever present, represents hydrogen, (C$_1$-C$_3$)alkyl or halo(C$_3$-C$_3$)alkyl;
R$_5$ and R$_6$ represents either hydrogen or methyl.
The present invention also provides methods for preparing, compositions comprising, and methods for using Compounds of Formula (I).

(ii) In another aspect, the invention relates to pharmaceutical compositions containing a therapeutically effective amount of at least one compound of formula (I), or individual stereoisomers, racemic or non-racemic mixture of stereoisomers, or pharmaceutically acceptable salts or solvates thereof; in admixture with at least one suitable carrier.

(iii) In another aspect, the invention relates to the use of a therapeutically effective amount of compound of formula (I), in manufacture of a medicament, for the treatment or prevention of a disorders involving selective affinity for the 5-HT$_6$ receptor.

(iv) In another aspect, the invention further relates to the process for preparing compounds of formula (I).

(v) Partial list of such compounds of general formula (I) is as follows
1-[3-(1-Methylpiperidin-4-yl)amino]benzenesulfonyl-1H-indole;

1-[3-(1-Methylpiperidin-4-yl)amino]benzenesulfonyl-5-methoxyindole;
1-[3-(1-Methylpiperidin-4-yl)amino]benzenesulfonyl-5-isopropoxyindole;
1-[3-(1-Methylpiperidin-4-yl)amino]benzenesulfonyl-5-Bromoindole;
1-[3-(1-Methylpiperidin-4-yl)amino]benzenesulfonyl-5-chloroindole;
1-[3-(1-Methylpiperidin-4-yl)amino]benzenesulfonyl-5-fluoroindole;
1-[3-(1-Methylpiperidin-4=yl)amino]benzenesulfonyl-4-chloroindole;
1-[3-(1-Methylpiperidin-4-yl)amino]benzenesulfonyl-6-chloroindole;
1-[3-(1-Methylpiperidin-4-yl)amino-4-methyl]benzenesulfonylindole;
1-[3-(1-Methylpiperidin-4-yl)amino-4-methyl]benzenesulfonyl-5-methoxyindole;
1-[3-(1-Methylpiperidin-4-yl)amino-4-methyl]benzenesulfonyl-5-isopropoxyindole;
1-[3-(1-Methylpiperidin-4-yl)amino-4-methyl]benzenesulfonyl-5-bromoindole;
1-[3-(1-Methylpiperidin-4-yl)amino-4-methyl]benzenesulfonyl-5-chloroindole;
1-[3-(1-Methylpiperidin-4-yl)amino-4-methyl]benzenesulfonyl-5-fluoroindole;
1-[3-(1-Methylpiperidin-4-yl)amino-4-methyl]benzenesulfonyl-4-chloroindole;
1-[3-(1-Methylpiperidin-4-yl)amino-4-methyl]benzenesulfonyl-6-chloroindole;
1-[3-(1-Methylpiperidin-4-yl)amino-4-methoxy]benzenesulfonyl-1H-indole;
1-[(3-(1-Methylpiperidin-4-yl)amino)-4-methoxy]benzenesulfonyl-5-methoxyindole;
1-[(3-(1-Methylpiperidin-4-yl)amino)-4-methoxy]benzenesulfonyl-5-isopropoxyindole;
1-[(3-(1-Methylpiperidin-4-yl)amino)-4-methoxy]benzenesulfonyl-5-bromoindole;
1-[(3-(1-Methylpiperidin-4-yl)amino)-4-methoxy]benzenesulfonyl-5-chloroindole;
1-[(3-(1-Methylpiperidin-4-yl)amino)-4-methoxy]benzenesulfonyl-5-fluoroindole;
1-[(3-(1-Methylpiperidin-4-yl)amino)-4-methoxy]benzenesulfonyl-4-chloroindole;
1-[(3-(1-Methylpiperidin-4-yl)amino)-4-methoxy]benzenesulfonyl-6-chloroindole;
1-[3-(1-Methylpiperidin-4-yl)amino-4-Fluoro]benzenesulfonylindole;
1-[3-(1-Methylpiperidin-4-yl)amino]benzenesulfonyl-3-bromoindole.
1-[3-(1-Methylpiperidin-4-yl)amino-4-methoxy]benzenesulfonyl-3-bromoindole.
1-[3-(1-Methylpiperidin-4-yl)amino]benzenesulfonyl-3-bromo-5-fluoroindole.
1-[3-(1-Methylpiperidin-4-yl)amino]benzenesulfonyl-3-bromo-4-chloroindole.
1-[3-(1-Methylpiperidin-4-yl)methylamino]benzenesulfonylindole.
1-[3-(1-Methylpiperidin-4-yl)methylamino]benzenesulfony-5-methoxy-indole.
1-[3-(1-Methylpiperidin-4-yl)methylamino]benzenesulfony-5-fluoroindole.
1-[3-(1-Methylpiperidin-4-yl)acetamido]benzenesulfony-5-fluoroindole.
1-[3-(1-Methylpiperidin-4-yl)acetamido]benzenesulfonyindole.
1-[3-(1-Methylpiperidin-4-yl)ethylamino]benzenesulfony-5-fluoroindole.
1-[3-(1-Methylpiperidin-4-yl)amino]benzenesulfonyl-5-fluoroindole Hydrochloride salt;
1-[3-(1-Methylpiperidin-4-yl)amino-4-methoxy]benzenesulfonyl-1H-indole Hydrochloride salt; a stereoisomer thereof and a salt thereof.

BRIEF DESCRIPTION OF THE ACCOMPANYING DRAWING

FIG. 1 shows a Bar graph demonstrating the effect of treatment of example 6 at 10 mg/Kg orally on the exploration time of animals with novel object, in comparison with the vehicle treated group.

FIG. 2 shows a graph demonstrating significant increase in latency to reach the dark zone at 10 mg/Kg oral dose.

DETAILED DESCRIPTION OF THE INVENTION

The 5-hydroxytryptamine-$_6$ (5-$HT_6$) receptor is one of the most recent receptors to be identified by molecular cloning. Its ability to bind a wide range of therapeutic compounds used in psychiatry, coupled with its intriguing distribution in the brain has stimulated significant interest in new compounds which are capable of interacting with or affecting said receptor.

Surprisingly, it has now been found that aminoaryl sulphonamide derivatives of formula (I) demonstrate 5-$HT_6$ receptor affinity,

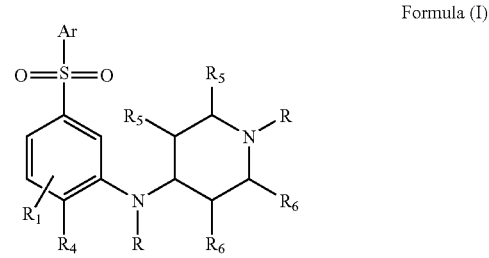

Formula (I)

wherein:
Ar represents any one group selected from phenyl, naphthyl, a monocyclic or bicyclic heteroaryl, each of which may be further substituted by one or more independent substituents and those substituents are defined as $R_1$;

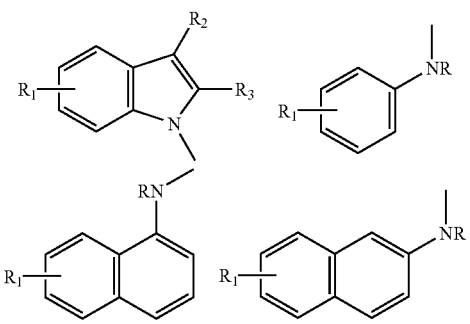

R represents either a hydrogen atom, ($C_1$-$C_3$)alkyl or halo ($C_1$-$C_3$)alkyl group;
$R_1$ and $R_4$ independently represents one or multiple substitutions on the benzene ring, and includes a hydrogen, halogen, cyano, $(C_1-C_3)$alkyl, halo$(C_1-C_3)$alkyl, $(C_1-C_3)$alkoxy, halo$(C_1-C_3)$alkoxy, cyclo$(C_3-C_6)$alkyl or cyclo$(C_3-C_6)$alkoxy;

$R_2$ whenever present, represents hydrogen, halogen, $(C_1-C_3)$alkyl, halo$(C_1-C_3)$alkyl, $(C_1-C_3)$alkoxy or halo$(C_1-C_3)$alkoxy;

$R_3$ whenever present, represents hydrogen, $(C_1-C_3)$alkyl or halo$(C_1-C_3)$alkyl;

$R_5$ and $R_6$ represents either hydrogen or methyl.

Each group of compound (I) is explained below. Each term used herein is defined to have meanings described below in either case of a single or a joint use with other terms, unless otherwise noted.

The term "halogen" as used herein and in the claims (unless the context indicates otherwise) means atom such as fluorine, chlorine, bromine or iodine;

The term "$(C_1-C_3)$alkyl" as used herein and in the claims (unless the context indicates otherwise) means straight and branched chain alkyl radicals containing from one to three carbon atoms and includes methyl, ethyl, n-propyl and iso-propyl.

The term "$(C_1-C_3)$alkoxy" as used herein and in the claims (unless the context indicates otherwise) means straight and branched chain alkyl radicals containing from one to three carbon atoms and includes methoxy, ethoxy, propyloxy and iso-propyloxy, which may be further substituted.

The term "halo$(C_1-C_3)$alkyl" as used herein and in the claims (unless the context indicates otherwise) means straight and branched chain alkyl radicals containing from one to three carbon atoms and includes fluoromethyl, difluoromethyl, trifluoromethyl, trifluoroethyl, fluoroethyl, difluoroethyl and the like.

The term "halo$(C_1-C_3)$alkoxy" as used herein and in the claims (unless the context indicates otherwise) means straight and branched chain alkyl radicals containing from one to three carbon atoms and includes fluoromethoxy, difluoromethoxy, trifluoromethoxy, trifluoroethoxy, fluoroethoxy, difludroethoxy and the like.

The term "cyclo$(C_3-C_6)$alkyl" as used herein and in the claims (unless the context indicates otherwise) means straight and branched chain alkyl radicals containing from three to six carbon atoms and includes cyclopropyl, cyclobutyl, cyclopentyl, cyclohexyl, the cycloalkyl group may be substituted.

The term "cyclo$(C_3-C_6)$alkoxy" as used herein and in the claims (unless the context indicates otherwise) means straight and branched chain alkyl radicals containing from three to six carbon atoms and includes cyclopropyloxy, cyclobutyloxy, cyclopentyloxy, cyclohexyloxy, the cycloalkoxy group may be substituted and the like.

The term "heteroaryl" is intended to mean a 5 or 6 membered monocyclic aromatic or a fused 8-10 membered bicyclic aromatic ring containing 1 to 3 heteroatoms selected from oxygen, nitrogen and sulphur. Suitable examples of such monocyclic aromatic rings include thienyl, furyl, pyrrolyl, triazolyl, imidazolyl, oxazolyl, thiazolyl, oxadiazolyl, isothiazolyl, isoxazolyl, thiadiazolyl, pyrazolyl, pyrimidyl, pyridazinyl, pyrazinyl and pyridyl. Suitable examples of such fused aromatic rings include benzofused aromatic rings such as quinolinyl, isoquinolinyl, quinazolinyl, quinoxalinyl, cinnolinyl, naphthyridinyl, indolyl, isoindolyl, indazolyl, pyrrolopyridinyl, benzofuranyl, isobenzofuranyl, benzothienyl, benzimidazolyl, benzoxazolyl, benzisoxazolyl, benzothiazolyl, benzisathiazolyl, benzoxadiazolyl, benzothiadiazolyl, benzotriazolyl and the like. Heteroaryl groups, as described above, may be linked to the remainder of the molecule via a carbon atom or, when present, a suitable nitrogen atom except where otherwise indicated above. It will be appreciated that wherein the above mentioned aryl or heteroaryl groups have more than one substituent, said substituents may be linked to form a ring, for example a carboxyl and amine group may be linked to form an amide group.

The term 5- to 7-membered heterocyclic ring is intended to mean a non aromatic ring containing 1 to 3 heteroatoms selected from oxygen, nitrogen and sulphur. Such rings may be partially unsaturated. Suitable examples of 5- to 7-membered heterocyclic rings include piperidinyl, tetrahydropyridinyl, pyrrolidinyl, morpholinyl, azepanyl, diazepanyl and piperazinyl. A 5- to 7-membered heterocyclic ring, as described above, may be linked to the remainder of the molecule via a carbon atom or a suitable nitrogen atom.

Certain compounds of formula (I) are capable of existing in stereoisomeric forms (e.g. diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

The term "stereoisomers" is a general term for all isomers of the individual molecules that differ only in the orientation of their atoms in space. It includes mirror image isomers (enantiomers), geometric (cis-trans) isomers and isomers of compounds with more than one chiral centre that are not mirror images of one another (diastereomers).

The stereoisomers as a rule are generally obtained as racemates that can be separated into the optically active isomers in a manner known per se. In the case of the compounds of general formula (I) having an asymmetric carbon atom the present invention relates to the D-form, the L-form and D,L-mixtures and in the case of a number of asymmetric carbon atoms, the diastereomeric forms and the invention extends to each of these stereoisomeric forms and to mixtures thereof including racemates. Those compounds of general formula (I) which have an asymmetric carbon and as a rule are obtained as racemates can be separated one from the other by the usual methods, or any given isomer may be obtained by stereospecific or asymmetric synthesis. However, it is also possible to employ an optically active compound from the start, a correspondingly optically active or diastereomeric compound then being obtained as the final compound.

The stereoisomers of compounds of general formula (I) may be prepared by one or more ways presented below:

i) One or more of the reagents may be used in their optically active form.

ii) Optically pure catalyst or chiral ligands along with metal catalyst may be employed in the reduction process. The metal catalysts may be employed in the reduction process. The metal catalyst may be Rhodium, Ruthenium, Indium and the like. The chiral ligands may preferably be chiral phosphines (Principles of Asymmetric synthesis, J. E. Baldwin Ed., Tetrahedron series, 14, 311-316).

iii) The mixture of stereoisomers may be resolved by conventional methods such as forming a diastereomeric salts with chiral acids or chiral amines, or chiral amino alcohols, chiral amino acids. The resulting mixture of diastereomers may then be separated by methods such as fractional crystallization, chromatography and the like, which is followed by an additional step of isolating the optically active product by hydrolyzing the derivative (Jacques et. al., "Enantiomers, Racemates and Resolution", Wiley Interscience, 1981).

iv) The mixture of stereoisomers may be resolved by conventional methods such as microbial resolution, resolving the diastereomeric salts formed with chiral acids or chiral bases.

Chiral acids that can be employed may be tartaric acid, mandelic acid, lactic acid, camphorsulfonic acid, amino acids and the like. Chiral bases that can be employed may be cinchona alkaloids, brucine or a basic amino group such as lysine, arginine and the like. In the case of the compounds of general formula (I) containing geometric isomerism the present invention relates to all of these geometric isomers.

Suitable pharmaceutically acceptable salts will be apparent to those skilled in the art and include those described in J. Pharm. Sci., 1977, 66, 1-19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. The present invention includes within its scope all possible stoichiometric and non-stoichiometric forms.

The pharmaceutically acceptable salts forming a part of this invention may be prepared by treating the compound of formula (I) with 1-6 equivalents of a base such as sodium hydride, sodium methoxide, sodium ethoxide, sodium hydroxide, potassium t-butoxide, calcium hydroxide, calcium acetate, calcium chloride, magnesium hydroxide, magnesium chloride and the like. Solvents such as water, acetone, ether, THF, methanol, ethanol, t-butanol, dioxane, isopropanol, isopropyl ether or mixtures thereof may be used.

In the addition to pharmaceutically acceptable salts, other salts are included in the invention. They may serve as intermediates in the purification of the compounds, in the preparation of other salts, or in the identification and characterization of the compounds or intermediates.

The compounds of formula (I) may be prepared in crystalline or non-crystalline form, and, if crystalline, may optionally be solvated, eg. as the hydrate. This invention includes within its scope stoichiometric solvates (eg. hydrates) as well as compounds containing variable amounts of solvent (eg. water).

The present invention also provides a process for the preparation of a compound of formula (I) or a pharmaceutically acceptable salt thereof, which comprises of contacting a compound of formula (a) wherein $R_1$, $R_4$ and Ar are as defined for the compound of formula (I) earlier, with a piperidone derivative of formula (b):

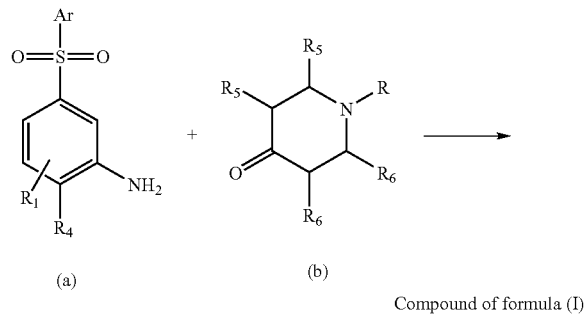

(a)          (b)

Compound of formula (I)

wherein, $R_5$, $R_6$ and R are as defined for the compound of formula (I) earlier; via reductive amination using a suitable reducing agent/catalyst in presence of inert solvent at ambient temperature to obtain a compound of formula (I).

The above reaction is preferably carried out in a solvent such as THF, toluene, acetone, ethyl acetate, DMF, DMSO, DME, N-methylpyrrolidone, methanol, ethanol propanol and the like and preferably using either acetone or DMF. The inert atmosphere may be maintained by using inert gases such as $N_2$, Ar or He. The reaction may be affected in the presence of a base such as $NaBH_4$, $NaBCNH_3$, Na(triacetoxy)BH and the like at ambient temperature, until the reaction is complete. A wide variety of basic agents can be used in this condensation. Optionally, other reagents such as titanium(IV)isopropoxide may be present. Reaction times of about 30 minutes to 72 hours are common. At the end of reaction, the volatile components are removed under reduced pressure. The reaction mixture can be optionally acidified before workup. The product can be isolated by precipitation, washed, dried and further purified by standard methods such as recrystallization, column chromatography etc.

Optionally compounds of formula (I) can be prepared by carrying out nucleophilic substitution in a compound of formula (a) wherein $R_1$, $R_4$ and Ar are as defined earlier, with a piperidinyl halide of formula (c): wherein $R_5$, $R_6$ and R are as defined above; X represents as

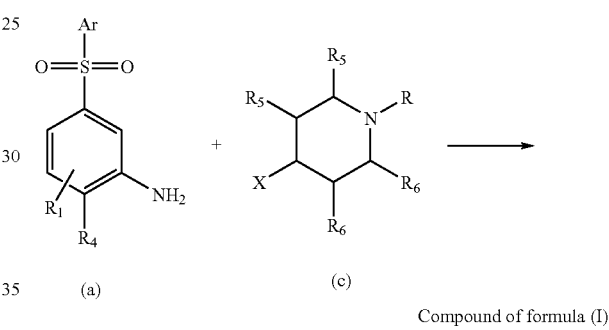

(a)          (c)

Compound of formula (I)

halogen atom (eg. fluoro, chloro or iodo); in presence of suitable base and inert solvent at suitable temperature to obtain a compound of formula (I).

The above reaction is preferably carried out in a solvent such as THF, toluene, ethyl acetate, acetone, water, DMF, DMSO, DME, and the like or a mixture thereof; and preferably using either acetone or DMF. The inert atmosphere may be maintained by using inert gases such as $N_2$, Ar or He. The reaction may be affected in the presence of a base such as $K_2CO_3$, $Na_2CO_3$, NaH or mixtures thereof. The reaction temperature may range from 20° C. to 150° C. based on the choice of solvent and preferably at a temperature in the range from 30° C. to 100° C. The duration of the reaction may range from 1 to 24 hours, preferably from 2 to 6 hours.

The intermediate compound (a) can be obtained by reacting indole derivative with Sulfonyl chlorides, $RSO_2Cl$, in the presence of an inert organic solvent which includes, aromatic hydrocarbons such as toluene, o-, m-, p-xylene; halogenated hydrocarbons such as methylene, chloride, chloroform, and chlorobenzene; ethers such as diethylether, diisopropyl ether, tert-butyl methyl ether, dioxane, anisole, and tetrahydrofuran; nitriles such as acetonitrile and propionitrile; ketones such as acetone, methyl ethyl ketone, diethyl ketone and tert-butyl methyl ketone; alcohols such as methanol, ethanol, n-propranol, n-butanol, tert-butanol and also DMF (N,N-dimethylformamide), DMSO(N,N-dimethyl sulfoxide) and water. The preferred list of solvents includes DMSO, DMF, acetonitrile and THF. Mixtures of these in varying ratios can also be used. Suitable bases are, generally, inorganic compounds such as alkali metal hydroxides and alkaline earth metal hydroxides, such as lithium hydroxide, sodium hydroxide, potassium hydroxide and calcium hydroxide; alkali metal oxides and alkaline earth metal oxides, lithium oxide, sodium oxide, magnesium oxide and calcium oxide; alkali metal hydrides and alkaline earth metal hydrides such as lithium hydride, sodium hydride, potassium hydride and calcium hydride; alkali metal amides and alkaline earth metal amides such as lithium amide, sodium amide, potassium amide and calcium amide; alkali metal carbonates and alkaline earth metal carbonates such as lithium carbonate and calcium carbonate; and also alkali metal hydrogen carbonates and alkaline earth metal hydrogen carbonates such as sodium hydrogen carbonate; organometallic compounds, particularly alkali metal alkyls such as methyl lithium, butyl lithium, phenyl lithium; alkyl magnesium halides such as methyl magnesium chloride, and alkali metal alkoxides and alkaline earth metal alkoxides such as sodium methoxide, sodium ethoxide, potassium ethoxide, potassium tert-butoxide and di-methoxymagnesium, further more organic bases e.g. triethylamine, triisopropylamine, and N-methylpiperidine, pyridine. Sodium hydroxide, Sodium methoxide, Sodium ethoxide, potassium hydroxide potassium carbonate and triethylamine are especially preferred. Suitably the reaction may be effected in the presence of phase transfer catalyst such as tetra-n-butylammonium hydrogensulphate and the like. The inert atmosphere may be maintained by using inert gases such as $N_2$, Ar or He. Reaction times may vary from 1 to 24 his, preferably from 2 to 6 hours, whereafter, if desired, the resulting compound is continued into a salt thereof. Sulfonyl chlorides, $R_{10}SO_2Cl$, may be obtained commercially or prepared by conventional techniques.

Compounds obtained by the above method of preparation of the present invention can be transferred to another compound of this invention by further chemical modifications of well-known reaction such as oxidation, reduction, protection, deprotection, rearrangement reaction, halogenation, hydroxylation, alkylation, alkylthiolation, demethylation, O-alkylation, O-acylation, N-alkylation, N-alkenylation, N-acylation, N-cyanation, N-sulfonylation, coupling reaction using transition metals and the like.

If necessary, any one or more than one of the following steps can be carried out, i) converting a compound of the formula (I) into another compound of the formula (I)

ii) removing any protecting groups; or iii) forming a pharmaceutically acceptable salt, solvate or a prodrug thereof.

In process (i), pharmaceutically acceptable salts may be prepared conventionally by reaction with the appropriate acid or acid derivative as described earlier in detail.

In process (ii), examples of protecting groups and the means for their removal can be found in T. W. Greene 'Protective Groups in Organic Synthesis' (J. Wiley and Sons, 1991). Suitable amine protecting groups include sulphonyl (e.g. tosyl), acyl (e.g. acetyl, 2', 2', 2'-trichloroethoxycarbonyl, benzyloxycarbonyl or t-butoxycarbonyl) and arylalkyl (e.g. benzyl), which may be removed by hydrolysis (e.g. using an acid such as hydrochloric or trifluoroacetic acid) or reductively (e.g. hydrogenolysis of a benzyl group or reductive removal of a 2', 2', 2'-trichloroethoxycarbonyl group using zinc in acetic acid) as appropriate. Other suitable amine protecting groups include trifluoroacetyl(—$COCF_3$) which may be removed by base catalysed hydrolysis or a solid phase resin bound benzyl group, such as a Merrifield resin bound 2,6-dimethoxybenzyl group (Ellman linker), which may be removed by acid catalysed hydrolysis, for example with trifluoroacetic acid.

Process (iii) may be performed using conventional interconversion procedures such as epimerisation, oxidation, reduction, alkylation, nucleophilic or electrophilic aromatic substitution, ester hydrolysis or amide bond formation.

In order to use the compounds of formula (I) in therapy, they will normally be formulated into a pharmaceutical composition in accordance with standard pharmaceutical practice.

The pharmaceutical compositions of the present invention may be formulated in a conventional manner using one or more pharmaceutically acceptable carriers. Thus, the active compounds of the invention may be formulated for oral, buccal, intranasal, parental (e.g., intravenous, intramuscular or subcutaneous) or rectal administration or a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of an aerosol spray from a pressurized container or a nebulizer, or from a capsule using a inhaler or insufflator. In the case of a pressurized aerosol, a suitable propellant, e.g., dichlorodifluoromethane, trichlorofluoromethane, dichlorotetrafluoroethane, carbon dioxide or other suitable gas and the dosage unit may be determined by providing a valve to deliver a metered amount. The medicament for pressurized container or nebulizer may contain a solution or suspension of the active compound while for a capsule it preferably should be in the form of powder. Capsules and cartridges (made, for example, from gelatin) for use in an inhaler or insufflator may be formulated containing a powder mix of a compound of the invention and a suitable powder base such as lactose or starch.

Aerosol formulations for treatment of the conditions referred to above (e.g., migraine) in the average adult human are preferably arranged so that each metered dose or "puff" of aerosol contains 20 µg to 1000 µg of the compound of the invention. The overall daily dose with an aerosol will be within the range 100 µg to 10 mg. Administration may be several times daily, for example 2, 3, 4 or 8 times, giving for example, 1, 2 or 3 doses each time.

An effective amount of a compound of general formula (I), or their derivatives as defined above can be used to produce a medicament, along with conventional pharmaceutical auxiliaries, carriers and additives.

Such therapy includes multiple choices: for example, administering two compatible compounds simultaneously in a single dose form or administering each compound individually in a separate dosage; or if required at same time interval or separately in order to maximize the beneficial effect or minimize the potential side-effects of the drugs according to the known principles of pharmacology.

The phrase "pharmaceutically acceptable" indicates that the substance or composition must be compatible chemically and/or toxicologically, with the other ingredients comprising a formulation, and/or the mammal being treated therewith.

The present compounds are useful as pharmaceuticals for the treatment of various conditions in which the use of a 5-$HT_6$ receptor antagonist is indicated, such as in the treatment of central nervous system disturbances such as psychosis, schizophrenia, manic depression, depression, neurological disturbances, memory disturbances. Parkinsonism, amylotrophic lateral sclerosis, Alzheimer's disease, Attention deficit hyperactivity disorder (ADHD) and Huntington's disease.

The term "schizophrenia" means schizophrenia, schizophreniform, disorder, schizoaffective disorder and psychotic disorder wherein the term "psychotic" refers to delusions, prominent hallucinations, disorganized speech or disorganized or catatonic behavior. See Diagnostic and Statistical Manual of Mental Disorder, fourth edition, American Psychiatric Association, Washington, D.C.

The terms "treating", "treat", or "treatment" embrace all the meanings such as preventative, prophylactic and palliative.

"Therapeutically effective amount" is defined as 'an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein'.

The dose of the active compounds can vary depending on factors such as the route of administration, age and weight of patient, nature and severity of the disease to be treated and similar factors. Therefore, any reference herein to a pharmacologically effective amount of the compounds of general formula (I) refers to the aforementioned factors. A proposed dose of the active compounds of this invention, for either oral, parenteral, nasal or buccal administration, to an average adult human, for the treatment of the conditions referred to above, is 0.1 to 200 mg of the active ingredient per unit dose which could be administered, for example, 1 to 4 times per day.

For illustrative purposes, the reaction scheme depicted herein provides potential routes for synthesizing the compounds of the present invention as well as key intermediates. For a more detailed description of the individual reaction steps, see the EXAMPLEs section. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Commercial reagents were utilized without further purification. Room temperature refers to 25-30° C. Melting points are uncorrected. IR spectra were taken using KBr and in solid state. Unless otherwise stated, all mass spectra were carried out using ESI conditions. $^1$H NMR spectra were recorded at 300 MHz on a Bruker instrument. Deuterated chloroform (99.8% D) was used as solvent. TMS was used as internal reference standard. Chemical shift values are expressed in are reported in parts per million (δ)-values. The following abbreviations are used for the multiplicity for the NMR signals: s=singlet, bs=broad singlet, d=doublet, t=triplet, q=quartet, qui=quintet, h=heptet, dd=double doublet, dt=double triplet, tt=triplet of triplets, m=multiplet. NMR, mass were corrected for background peaks. Specific rotations were measured at room temperature using the sodium D (589 nm). Chromatography refers to column chromatography performed using 60-120 mesh silica gel and executed under nitrogen pressure (flash chromatography) conditions.

All publications, including but not limited to patents and patent applications, cited in this specification are herein incorporated by reference as if each individual publication were specifically and individually indicated to be incorporated by reference herein as though fully set forth.

The following Descriptions mid EXAMPLEs illustrate the preparation of compounds of the invention.

Description 1:

3-Nitrobenzenesulfonyl chloride (D1)

Chlorosulfonic acid (475 g) was taken in a 1 L three neck round bottom flask equipped with a guard tube and liquid addition funnel. Chlorosulfonic acid was cooled in an ice bath to 5-10° C. and nitrobenzene was added to the acid slowly, at such a rate that the temperature is maintained below 10° C. Reaction mixture was then brought to 25° C. and then slowly heated in an oil bath to 80-85° C. Reaction mixture was stirred further at 80-85° C. for 3 hours. After the completion of reaction (TLC), the reaction mixture was cooled to 10° C. and poured onto the ice-water mixture along with stirring and maintaining the temperature below 10° C.; the resulting slurry is then filtered on buchner funnel. Solid cake on funnel is washed with 500 mL of water. Resulting solid cake is dried on phosphorous pentoxide in a desiccator to obtain the D1 as off white solid.

Description 2:

1-(3-Nitro)benzenesulfonylindole (D2)

To a solution of indole (17.09 mmoles, 2.0 g) in 20 mL of 1,2-dichloroethane in 100 mL three necked round bottomed flask, was added (34.19 mmoles, 3.45 g) of triethylamine at 25° C. To the above mixture was added a solution of 3-nitrobenzenesulfonylchloride (25.64 mmols, 5.68 g) in 25 ml. dichloromethane, maintaining the temperature below 10° C. The reaction mixture was then stirred for 24 hours at 25° C. After the completion of reaction (TLC), the reaction mixture was poured on ice-water mixture along with stirring and the resulting mixture was extracted with ethyl acetate (2×30 mL). The combined ethyl acetate extracts were then washed with water, brine and dried over anhydrous magnesium sulfate. The volatiles were removed under the reduced pressure to obtain 5.4 g of crude thick oil. This compound was purified on column using acidic silica and n-hexane to 5% ethylacetate: n-hexane as eluent.

Description 3:

1-(3-Aminobenzenesulfonyl)indole (D3)

To a solution of 1-(3-Nitrobenzenesulfonyl)indole (6.62 mmoles, 2.0 g) in 10 mL of ethanol in 50 mL three necked round bottomed flask, was added (33.11 mmoles, 1.85 g) of iron powder at 25° C. To the above mixture was added 2 mL water and 1-2 drops of hydrochloric acid. The reaction mixture was then stirred for 4 hour at 75-80° C. After the completion of reaction (TLC), the reaction mixture was filtered through buchner funnel and residue was washed with 20 mL×2 portions of hot ethanol. Combined ethanol layer was distilled under vacuum, the residue was quenched in 30 mL ice-cold water and basified with 40% sodium hydroxide solution. Aqueous layer was extracted with dichloromethane (50 mL×3). The combined dichloromethane extracts were then washed with water, brine and dried over anhydrous magnesium sulfate. The volatiles were removed under the reduced pressure to obtain 2.4 g crude thick oil. This compound was purified on column using neutral silica and n-hexane to 40% ethylacetate:n-hexane as eluent.

Description 4:

N-acetyl-2-anisidine

Ortho anisidine (0.67 moles, 82 g.) was taken in a 1 L round bottom flask equipped with a liquid addition funnel and a guard tube; triethylamine (1.0 mole, 100 g) was added to it in one lot. Above mixture was cooled to 0-5° C. and acetyl chloride was added drop-wise maintaining temperature below 10° C. After addition of acetyl chloride cooling was removed and the reaction mixture was stirred at 25-28° C. for 0.3 hours. After the completion of reaction (TLC), the reaction mixture was poured on ice-water, and aqueous layer was extracted with dichloromethane (2×300 mL). The combined dichloromethane extracts were then washed with water, brine and dried over anhydrous magnesium sulfate. The volatiles were removed under the reduced pressure to obtain 96.5 g. of solid.

Description 5:

3-Acetamido-4-methoxybenzenesulfonyl chloride

Chlorosulfonic acid (475 g.) was taken in a three neck round bottom flask equipped with a guard tube and cooled to 10° C. 2-Methoxy acetanilide (95 g.) was added in small portions maintaining temperature below 10° C. After complete addition of 2-methoxy acetanilide, cooling was removed and reaction was brought to 25° C. Reaction mixture was stirred at 25° C. for further 24 hours. After the completion of reaction (TLC), the reaction mixture was poured on ice-water mixture and the resulting slurry was filtered on buchner funnel. Solid cake on funnel was washed with 500 mL of water and the resulting solid is dried on phosphorus pentoxide in a desiccator to give 114.5 grams off white solid.

Description 6:

1-(3-Acetamido-4-methoxy)benzenesulfonyl indole

Indole (17.09 mmoles, 2.0 g.) was taken in a 100 mL 3 necked round bottomed flask, along with N,N-dimethyl formamide (20 mL). The above solution was then added slowly to a suspension of sodium hydride (25.64 mmoles, 1.02 g.) in DMF, maintaining the temperature below 10° C. The reaction mixture was then stirred for 1 hour at 25° C. To this well stirred solution was then added the 3-(N-acetyl)-4-methoxy-benzenesulfonyl chloride (22.22 mmoles, 5.86 g), slowly, at such a rate, that the temperature is maintained below 10° C. The reaction mixture was further stirred for 2 hours. After the completion of reaction (TLC), the reaction mixture was poured on 100 g of ice-water mixture along with stirring and the resulting mixture was extracted with ethyl acetate (2×30 mL). The combined ethyl acetate extracts were then washed with water, brine and dried over anhydrous magnesium sulfate. The volatiles were removed under the reduced pressure to obtain 6.52 g. crude thick oil.

Description 7:

1-(3-Amino-4-methoxy)benzenesulfonyl indole 1-(3-acetylamino)benzenesulfonyl-1H-indole (18.95 mmoles, 6.52 g.) was taken in a 50 ml. three neck round bottom flask with 15 mL ethanol. Above solution was heated on oil bath to 50-55° C. and hydrochloric acid (47.38=moles, 5.76 g, 30% purity) was added dropwise. Reaction mixture was refluxed at 80-85° C. for 3 hours. After the completion of reaction (TLC), the reaction mixture was poured on 60 g of ice-water, basified with 20% NaOH solution and mixture was extracted with ethyl acetate (2×60 mL). The combined ethyl acetate extracts were then washed with water, brine and dried over anhydrous Magnesium sulfate. The volatiles were removed under the reduced pressure to obtain crude thick oil. The compound was purified over Silica gel column with ethyl acetate and n-hexane (5 to 30%) as eluents to obtain 3.2 grams of white solid.

Description 8:

N-acetyl-2-toluidine

Ortho toluidine (0.75 moles, 80 g.) was taken in a one liter round bottom flask equipped with a liquid addition funnel and a guard tube. Triethylamine (1.13 moles, 113.77 g.) was added to it in one lot. Above mixture was cooled to 0-5° C. and acetyl chloride was added drop-wise maintaining the temperature below 10° C. After addition of acetyl chloride the cooling was removed and reaction was stirred at 25-28° C. for 3 hours. After the completion of reaction (TLC), the reaction mixture was poured on 500 g. of ice-water, and aqueous layer was extracted with dichloromethane (2×300 mL). The combined dichloromethane extracts were then washed with water, brine and dried over anhydrous magnesium sulfate. The volatiles were removed under the reduced pressure to obtain 113.6 grams solid.

Description 9:

3-Acetamido-4-methylbenzenesulfonyl chloride

Chlorosulfonic acid (500 g.) was taken in a three neck round bottom flask equipped with a guard tube and cooled it to 10° C. N-acetyl 2-toluidine (100 g.) was added in small portions maintaining temperature below 10° C. After complete addition of 2-methoxy acetanilide cooling is removed and reaction was brought to 25° C. Reaction mixture was stirred at 25° C. for further 24 hours. After the completion of reaction (TLC), the reaction mixture was poured on ice-water, and the resulting slurry was filtered on buchner funnel. Solid cake on funnel was washed with 500 mL of water and the resulting solid was dried on phosphorus pentoxide in a desiccator to obtain 113.5 grams off white solid. It was found to contain a mixture of two isomers as confirmed from NMR and HPLC; however the desired isomer was obtained by partial crystallization using benzene and used for further experimentation, after the thorough carectorisation.

Description 10:

1-(3-Acetamido-4-methyl)benzenesulfonyl indole

Indole (17.09 mmoles, 2.0 g) was taken in a 100 mL 3 necked round bottomed flask, along with N,N-dimethyl formamide (20 mL). The above solution was then added slowly to a suspension of sodium hydride (25.64=moles, 1.02 g) in DMF maintaining the temperature below 10° C. The reaction mixture was then stirred for 1 hour at 25° C. To this well stirred solution was then added the 3-(N-acetyl)-4-methyl-benzenesulfonyl chloride (22.22 mmoles, 5.86 g), slowly, maintaining the temperature below 10° C. The reaction mixture was further stirred for 2 hours. After the completion of reaction (TLC), the reaction mixture was poured on ice-water mixture along with stirring and the resulting mixture was extracted with ethyl acetate (2×30 mL). The combined ethyl acetate extracts were then washed with water, brine and dried over anhydrous magnesium sulfate. The volatiles were removed under the reduced pressure to obtain 5.8 g crude thick oil. The compound was purified over Silica gel column with ethyl acetate and n-hexane (5 to 50%) as eluents to give 1.3 g of sticky solid.

Description 11:

1-(3-amino-4-methyl)benzenesulfonyl indole 1-(3-(N-acetamido)-4-methyl)benzenesulfonyl-1H-indole (3.96 mmoles, 1.3 g) was taken in a 50 mL three necked round bottom flask with 3 mL ethanol. Above solution was heated on oil bath to 50-55° C. and hydrochloric acid (9.9 mmoles, 1.21 g, 30% purity) is added drop-wise. Reaction mixture was refluxed at 80-85° C. for 3 hours. After the completion of reaction (TLC), the reaction mixture was poured on ice-water, basified with 40% NaOH solution and mixture was extracted with ethyl acetate (2×60 mL). The combined ethyl acetate extracts were then washed with water, brine and dried over anhydrous magnesium sulfate. The volatiles were removed under the reduced pressure to obtain 1.5 g. crude thick oil.

EXAMPLE 1

1-[3-(1-Methylpiperidin-4-yl)amino]benzenesulfonyl-1H-indole

To the solution of 1-(3-aminobenzenesulfonyl)indole (4.49 mmoles, 1.0 g.) in 20 mL acetic acid was added N-methyl 4-piperidone (8.99 mmoles, 1.01 g.) and sodium sulphate (44.98=moles, 6.388 g.) at 10° C. The reaction mixture was stirred at 25° C. for 1 hour. After 1 hour, sodium triacetoxyborohydride (13.47 mmoles, 3.3 g.) in small portions within a period of 30 minutes, after complete addition of sodium triacetoxyborohydride reaction is stirred at 250° C. for 24 hours. After the completion of reaction (TLC), the reaction mixture was poured on ice-water mixture, basified with 20% NaOH solution and mixture was extracted with ethyl acetate (2×60 mL). The combined ethyl acetate extracts were then washed with water, brine and dried over anhydrous magnesium sulfate. The volatiles were removed under the reduced pressure to obtain crude thick oil. The compound was purified over Silica gel column with Ethyl acetate and triethylamine (0.2 to 1.0%) as eluents to give 494 mg. of crystalline solid. IR spectra ($Cm^{-1}$): 1129, 1172, 1600, 2940, 3406; Mass (m/z): 370.3 $(M+H)^+$; $^1$H-NMR (δ, ppm): 1.40-1.46 (2H, m), 1.89-1.93 (21-1, m), 2.07-2.12 (2H, m), 2.30 (3H, s), 2.76-2.79 (2H, d, J=11.48 Hz), 3.17-3.19 (1H, m), 3.77-3.79 (1H, d, J=7.76 Hz), 6.64-6.65 (2H, m), 6.95-6.96 (1H, t, J=1.96 and 1.84 Hz), 7.12-7.13 (2H, m), 7.22-7.32 (2H, m), 7.52-7.54 (2H, m), 7.99-8.01 (1H, d, J=8.28 Hz).

EXAMPLE 2

1-[3-(1-Methylpiperidin-4-yl)amino]benzenesulfonyl-5-methoxyindole

Using a similar procedure as given in the preparation of EXAMPLE 1 and some non-critical variations above derivative was prepared. IR spectra ($Cm^{-1}$): 1145, 1225, 1336, 3374; Mass (m/z): 400.4 $(M+H)^+$; $^1$H-NMR (δ, ppm): 1.39-1.48 (2H, m), 1.90-1.97 (2H, m), 2.09-2.17 (2H, m), 2.32 (3H, s), 2.79-2.82 (2H, m), 3.18-3.2 (1H, m), 3.75-3.77 (1H, d, J=7.74 Hz), 3.81 (3H, s), 6.57-6.58 (1H, d, J=3.66 Hz), 6.61-6.66 (1H, m), 6.90-6.93 (2H, m), 6.97-6.979 (1H, d, J=2.416 Hz), 7.098-7.18 (2H, m), 7.482-7.491 (1H, d, J=3.65 Hz), 7.881-7.9 (1H, d, J=9.1 Hz).

EXAMPLE 3

1-[3-(1-Methylpiperidin-4-yl)amino]benzenesulfonyl-5-isopropoxyindole

Using a similar procedure as given in the preparation of EXAMPLE 1 and some non-critical variations above derivative was prepared. IR spectra ($Cm^{-1}$): 1147, 1455, 1601, 2936, 3403; Mass (m/z): 428.4 $(M+H)^+$; $^1$H-NMR (δ, ppm): 1.31-1.33 (d, 6H, J=6.07 Hz), 1.41-1.47 (2H, m), 1.9-1.93 (2H, d, J=12.06 Hz), 2.08-2.14 (2H, m), 2.31 (3H, s), 2.79-2.81 (2H, d, J=11.32 Hz), 3.18-3.2 (1H, m), 3.76-3.78 (1H, d, J=7.71 Hz), 4.48-4.52 (q, 1H), 6.55-6.55 (1H, d, J=3.58 Hz), 6.63-6.66 (1H, dd), 6.88-6.91 (1H, d, J=2.43, 2.4 and 9.0 Hz), 6.92-6.92 (1H, t, J=1.82 and 1.62 Hz), 6.97-6.98 (1H, d, J=2.34 Hz), 7.07-7.18 (2H, m), 7.46-7.47 (1H, d, J=3.6 Hz), 7.86-7.88 (1H, d, J=9.03 Hz),

EXAMPLE 4

1-[3-(1-Methylpiperidin-4-yl)amino]benzenesulfonyl-5-bromoindole

Using a similar procedure as given in the preparation of EXAMPLE 1 and some non-critical variations above derivative was prepared. IR spectra ($Cm^{-1}$): 1129, 1600, 2936, 3254; Mass (m/z): 448, 450 $(M+H)^+$; $^1$H-NMR (δ, ppm): 1.42-1.47 (2H, m), 1.89-1.93 (2H, m), 2.08-2.14 (2H, m), 2.32 (3H, s), 2.79-2.82 (2H, d, J=11.52 Hz), 3.17-3.19 (1H, m), 3.79-3.81 (1H, d, J=7.84 Hz), 6.58-6.59 (1H, d, J=3.64 Hz), 6.65-6.69 (1H, dd), 6.89-6.9 (1H, t, J=2.08 and 2.0 Hz), 7.65-7.11 (1H, m), 7.15-7.18 (1H, t, J=8.0 and 7.92 Hz), 7.38-7.41 (1H, dd, J=1.92 and 8.8 Hz), 7.52-7.53 (1H, d, J=3.68 Hz), 7.66-7.67 (1H, d, J=1.88 Hz), 7.87-7.89 (1H, d, J=8.8 Hz).

EXAMPLE 5

1-[3-(1-Methylpiperidin-4-yl)amino]benzenesulfonyl-5-chloroindole

Using a similar procedure as given in the preparation of EXAMPLE 1 and some non-critical variations above derivative was prepared. IR spectra ($Cm^{-1}$): 1130, 1367, 1600, 2939, 3255; Mass (m/z): 404.3, 406.3 $(M+H)^+$; $^1$H-NMR ($\delta$, ppm): 1.39-1.48 (2H, m), 1.89-1.92 (2H, d, J=12.2 Hz), 2.08-2.14 (2H, m), 2.31 (3H, s), 2.79-2.82 (2H, d, J=11.6 Hz), 3.17-3.18 (1H, m), 3.79-3.81 (1H, d, J=6.88 Hz), 6.58-6.59 (1H, d, J=3.72 Hz), 6.67-6.68 (1H, d, J=2.2 Hz), 6.9-6.91 (1H, t, J=2.0 and 1.76 Hz), 7.07-7.19 (2H, m), 7.24-7.27 (1H, dd, J=2.0 and 8.8 Hz), 7.5-7.5 (1H, d, J=1.96 Hz), 7.54-7.55 (1H, d, J=3.64 Hz), 7.91-7.94 (1H, d, J=8.84 Hz).

EXAMPLE 6

1-[3-(1-Methylpiperidin-4-yl)amino]benzenesulfonyl-5-fluoroindole

Using a similar procedure as given in the preparation of EXAMPLE 1 and some non-critical variations above derivative was prepared. IR spectra ($Cm^{-1}$): 1139, 1363, 1693, 2933, 3265; Mass (m/z): 388.3 $(M+H)^+$; $^1$H-NMR ($\delta$, ppm): 1.38-1.47 (2H, m), 1.89-1.93 (2H, m), 2.07-2.12 (2H, m), 2.3 (3H, s), 2.77-2.8 (2H, d, J=11.52 Hz), 3.17-3.22 (1H, m), 3.8-3.82 (1H, d, J=7.82 Hz), 6.6-6.61 (1H, d, J=3.97 Hz), 6.65-6.69 (1H, d), 6.91-6.92 (1H, t, J=2 Hz), 7.09-7.19 (4H, m), 7.56-7.57 (1H, d, J=3.65 Hz), 7.92-7.96 (1H, m).

EXAMPLE 7

1-[3-(1-Methylpiperidin-4-yl)amino]benzenesulfonyl-4-chloroindole

Using a similar procedure as given in the preparation of EXAMPLE 1 and some non-critical variations above derivative was prepared. IR spectra ($Cm^{-1}$): 1135, 1475, 1600, 2935, 3252; Mass (m/z): 404.3, 406.3 $(M+H)^+$; $^1$H-NMR ($\delta$, ppm): 1.38-1.47 (2H, m), 1.9-1.93 (2H, m), 2.09-2.17 (2H, m), 2.32 (3H, s), 2.77-2.8 (1H, d, J=11.6 Hz), 3.15-3.22 (1H, m), 3.79-3.81 (1H, d, J=7.76 Hz), 6.66-6.68 (1H, dd, J=1.64, 1.56 and 8.0 Hz), 6.77-6.77 (1H, d, J=3.64 Hz), 6.92-6.93 (1H, t, J=1.96 and 1.88 Hz), 7.09-7.23 (4H, m), 7.58-7.59 (1H, d, J=3.72 Hz), 7.88-7.93 (1H, m).

EXAMPLE 8

1-[3-(1-Methylpiperidin-4-yl)amino]benzenesulfonyl-6-chloroindole

Using a similar procedure as given in the preparation of EXAMPLE 1 and some non-critical variations above derivative was prepared. IR spectra ($Cm^{-1}$): 1128, 1176, 1510, 1601, 3415; Mass (m/z): 404.3, 406.3 $(M+H)^+$; $^1$H-NMR ($\delta$, ppm): 1.41-1.49 (2H, m), 1.92-1.96 (2H, m), 2.11-2.16 (2H, m), 2.31 (3H, s), 2.79-2.82 (2H, d, J=11.48 Hz), 3.21-3.23 (1H, m), 3.83-3.85 (1H, d, J=7.68 Hz), 6.6-6.61 (1H, d, J=3.6 Hz), 6.65-6.69 (1H, dd), 6.97-6.98 (1H, t, J=2.04 and 1.92 Hz), 7.08-7.22 (3H, m), 7.42-7.44 (1H, d, J=8.36 Hz), 7.51-7.52 (1H, d, J=3.68 Hz), 8.03-8.03 (1H, d, J=1.24 Hz),

EXAMPLE 9

1-[3-(1-Methylpiperidin-4-yl)amino-4-methyl]benzenesulfonylindole

Using a similar procedure as given in the preparation of EXAMPLE 1 and some non-critical variations above derivative was prepared. IR spectra ($Cm^{-1}$): 1133, 1170, 1365, 1516, 2933, 3428; Mass (m/z): 384.3 $(M+H)^+$; $^1$H-NMR ($\delta$, ppm): 1.36-1.45 (2H, m), 1.88-1.92 (2H, m), 2.04 (3H, s), 2.11-2.11 (2H, t, J=11.0 and 10.32), 2.32 (3H, s), 2.76-2.79 (2H, d, J=11.28 Hz), 3.19-3.28 (1H, m), 3.48-3.5 (1H, d, J=7.36 Hz), 6.62-6.63 (1H, d, J=3.76 Hz), 6.90-6.91 (1H, d, J=1.72 Hz), 7.03-7.05 (1H, d, J=7.84 Hz), 7.08-7.12 (1H, dd), 7.18-7.31 (2H, m), 7.5-7.55 (2H, m), 8.01-8.03 (1H, d, J=8.32 Hz)

EXAMPLE 10

1-[3-(1-Methylpiperidin-4-yl)amino-4-methyl]benzenesulfonyl-5-methoxyindole

Using a similar procedure as given in the preparation of EXAMPLE 1 and some non-critical variations above derivative was prepared. IR spectra ($Cm^{-1}$): 1147, 1364, 1467, 1928, 3412; Mass (m/z): 414.4 $(M+H)^+$; $^1$H-NMR (ppm): 1.42-1.48 (2H, m), 1.88-1.92 (2H, m), 2.04 (3H, s), 2.1-2.17 (2H, m), 2.35 (3H, s), 2.81-2.84 (2H, t, J=10 Hz), 3.19-3.28 (2H, m), 3.47-3.52 (1H, m), 3.81 (3H, s), 6.55-6.56 (1H, d, J=3.56 Hz), 6.86-6.86 (1H, d, J=1.52 Hz), 6.88-6.91 (1H, dd, J=2.52, 2.48 and 9.02 Hz), 6.96-6.96 (1N, d, J=2.48 Hz), 7.02-7.04 (1H, d, J=7.88 Hz), 7.066-7.09 (1H, dd, J=1.68, 1.72 and 7.82 Hz), 7.477-7.486 (1H, d, J=3.6 Hz), 7.9-7.92 (1H, d, J=8.96 Hz).

EXAMPLE 11

1-[3-(1-Methylpiperidin-4-yl)amino-4-methyl]benzenesulfonyl-5-isopropoxyindole

Using a similar procedure as given in the preparation of EXAMPLE 1 and some non-critical variations above derivative was prepared. Mass (m/z): 443 $(M+H)^+$

EXAMPLE 12

1-[3-(1-Methylpiperidin-4-yl)amino-4-methyl]benzenesulfonyl-5-bromoindole

Using a similar procedure as given in the preparation of EXAMPLE 1 and some non-critical variations above derivative was prepared. IR spectra ($Cm^{-1}$): 1129, 1368, 1439, 1680, 2936, 3419; Mass (m/z): 462.2, 464.2 $(M+H)^+$; $^1$H-NMR ($\delta$, ppm): 1.38-1.49 (2H, m), 1.84-1.92 (2H, m), 2.05 (3H, s), 2.14-2.17 (2H, m), 2.34 (3H, s), 2.8-2.84 (2H, m), 3.16-3.22 (1H, m), 3.49-3.55 (1H, m), 6.57-6.57 (1H, d, J=3.53 Hz), 6.83-6.84 (1H, d, J=1.26 Hz), 7.04-7.07 (2H, m), 7.37-7.4 (1H, dd, J=1.92 and 8.8 Hz), 7.52-7.53 (1H, d, J=3.64 Hz), 7.65-7.66 (1H, d, J=1.87 Hz), 7.89-7.92 (1H, d, J=8.8 Hz).

EXAMPLE 13

1-[3-(1-Methylpiperidin-4-yl)amino-4-methyl]benzenesulfonyl-5-chloroindole

Using a similar procedure as given in the preparation of EXAMPLE 1 and some non-critical variations above derivative was prepared. Mass (m/z): 419 (M+H)$^+$, 421 (M+H)$^+$

EXAMPLE 14

1-[3-(1-Methylpiperidin-4-yl)amino-4-methyl]benzenesulfonyl-5-fluoroindole

Using a similar procedure as given in the preparation of EXAMPLE 1 and some non-critical variations above derivative was prepared. IR spectra (Cm$^{-1}$): 1138, 1170, 1367, 1459, 2940, 3422; Mass (m/z): 402.3 (M+H)$^+$; $^1$H-NMR (δ, ppm): 1.39-1.46 (21-1, m), 1.88-1.91 (2H, m), 2.05 (3H, s), 2.11-2.16 (2H, m), 2.33 (3H, s), 2.78-2.8 (2H, d, J=11.1 Hz), 3.17-3.28 (1H, m), 3.51-3.52 (1H, d, J=7.1 Hz), 6.58-6.59 (1H, d, J=3.68 Hz), 6.83-6.87 (1H, m), 6.98-7.1 (3H, m), 7.15-7.18 (1H, dd, J=2.5 and 8.77 Hz), 7.56-7.56 (1H, d, J=3.61 Hz), 7.94-7.98 (1H, dd, J=4.65, 4.39 and 9.06 Hz).

EXAMPLE 15

1-[3-(1-Methylpiperidin-4-yl)amino-4-methyl]benzenesulfonyl-4-chloroindole

Using a similar procedure as given in the preparation of EXAMPLE 1 and some non-critical variations above derivative was prepared. Mass (m/z): 419 (M+H)$^+$, 421 (M+H)$^+$

EXAMPLE 16

1-[3-(1-Methylpiperidin-4-yl)amino-4-methyl]benzenesulfonyl-6-chloroindole

Using a similar procedure as given in the preparation of EXAMPLE 1 and some non-critical variations above derivative was prepared. Mass (m/z): 419 (M+H)$^+$, 421 (M+H)$^+$

EXAMPLE 17

1-[3-(1-Methylpiperidin-4-yl)amino-4-methoxy]benzenesulfonyl-1H-indole

Using a similar procedure as given in the preparation of EXAMPLE 1 and some non-critical variations above derivative was prepared IR spectra (Cm$^{-1}$): 1130, 1165, 1525, 2937, 3412; Mass (m/z): 398.4 (M−H)$^+$; $^1$H-NMR (δ, ppm): 1.35-1.45 (2H, m), 1.86-1.89 (2H, m), 2.08-2.14 (2H, m), 2.31 (3H, s), 2.75-2.78 (2H, d, J=11.36 Hz), 3.15-3.2 (1H, m), 3.8 (3H, s), 4.2-4.22 (1H, d, J=7.92 Hz), 6.61-6.62 (1H, d, J=3.6 Hz), 6.65-6.68 (1H, d, J=8.48 Hz), 6.86-6.87 (1H, d, J=2.24 Hz), 7.18-7.22 (2H, m), 7.26-7.28 (1H, m), 7.5-7.53 (2H, m), 8.01-8.03 (1H, d, J=8.2 Hz).

EXAMPLE 18

1-[(3-(1-Methylpiperidin-4-yl)amino)-4-methoxy]benzenesulfonyl-5-methoxyindole

Using a similar procedure as given in the preparation of EXAMPLE 1 and some non-critical variations above derivative was prepared. IR spectra (Cm$^{-1}$): 1148, 1169, 1521, 2941, 3400; Mass (m/z): 430.3 (M+H)$^+$; $^1$H-NMR (δ, ppm): 1.37-1.46 (2H, m), 1.86-1.9 (2H, m), 2.1-2.16 (2H, m), 2.33 (3H, s), 2.782-2.811 (2H, m), 3.152-3.171 (1H, m), 3.808-3.815 (611, d), 4.2-4.22 (1H, d, J=7.91 Hz), 6.54-6.55 (1H, d, J=3.62 Hz), 6.65-6.67 (1H, d, J=8.47 Hz), 6.82-6.83 (1H, d, J=2.22 Hz), 6.88-6.91 (1H, dd, J=2.48 and 9.02 Hz), 6.95-6.96 (1H, d, J=2.25 Hz), 7.15-7.18 (1H, dd, J=2.25 and 8.42 Hz), 7.47-7.48 (1H, d, J=3.59 Hz), 7.9-7.92 (1H, d, J=8.96 Hz).

EXAMPLE 19

1-[3-(1-Methylpiperidin-4-yl)amino)-4-methoxy]benzenesulfonyl-5-isopropoxyindole Using a similar procedure as given in the preparation of EXAMPLE 1 and some non-critical variations above derivative was prepared. IR spectra (Cm$^{-1}$): 1147, 1454, 1519, 2937, 3403; Mass (m/z): 457.8 (M+H)$^+$; $^1$H-NMR (δ, ppm): 1.31-1.32 (d, 611, J=6.08 Hz), 1.39-1.44 (2H, m), 1.86-1.89 (2H, m), 2.08-2.14 (2H, m), 2.31 (3H, s), 2.76-2.79 (2H, m), 3.15-3.17 (1H, m), 3.81 (3H, s), 4.2-4.22 (1H, d J=7.84 Hz), 4.47-4.53 (q, 1H), 6.52-6.53 (1H, d, J=3.6 Hz), 6.65-6.67 (1H, d, J=8.52 Hz), 6.83-6.84 (1H, d, J=2.2 Hz), 6.86-6.89 (1H, dd, J=2.44 and 8.98 Hz), 6.95-6.96 (1H, d, J=2.4 Hz), 7.16-7.18 (1H, dd, J=2.24 and 8.4 Hz), 7.46-7.47 (1H, d, J=3.6 Hz), 7.88-7.9 (1H, d, J=9.0 Hz).

EXAMPLE 20

1-[(3-(1-Methylpiperidin-4-yl)amino)-4-methoxy]benzenesulfonyl-5-bromoindole

Using a similar procedure as given in the preparation of EXAMPLE 1 and some non-critical variations above derivative was prepared. $^1$H-NMR (δ, ppm): 1.39-1.45 (2H, m), 1.84-1.88 (2H, m), 2.07-2.13 (2H, m), 2.32 (3H, s), 2.77-2.83 (2H, m), 3.13-3.15 (1H, m), 3.81 (3H, s), 4.24-4.26 (1H, d, J=7.88 Hz), 6.55-6.55 (1H, d, J=3.76 Hz), 6.66-6.68 (1H, d, J=8.44 Hz), 6.79-6.8 (1H, d, J=2.24 Hz), 7.16-7.19 (1H, dd, J=2.28 and 8.4 Hz), 7.36-7.39 (1H, dd, J=1.92 and 8.8 Hz), 7.52-7.53 (1H, d, J=3.68 Hz), 7.64-7.64 (1H, d, J=1.88 Hz), 7.89-7.92 (1H, d, J=8.84 Hz).

EXAMPLE 21

1-[(3-(1-Methylpiperidin-4-yl)amino)-4-methoxy]benzenesulfonyl-5-chloroindole

Using a similar procedure as given in the preparation of EXAMPLE 1 and some non-critical variations above derivative was prepared. IR spectra (Cm$^{-1}$): 1129, 1166, 1519, 2940, 3418; Mass (m/z): 434.4 (M+H)$^4$, 436.4 (M+2)$^+$; $^1$H-NMR (δ, ppm): 1.38-1.44 (2H, m), 1.85-1.89 (2H, d), 2.09-2.15 (2H, m), 2.33 (3H, s), 2.79-2.81 (2H, m), 3.09-3.20 (1H, m), 3.82 (3H, s), 4.23-4.25 (1H, d, J=7.84 Hz), 6.55-6.56 (1H, m), 6.67-6.69 (1H, d, J=8.48 Hz), 6.8-6.81 (1H, d, J=2.28 Hz), 7.16-7.19 (1H, dd, J=2.4, 2.32 and 8.48 Hz), 7.23-726 (1H, m), 7.48-7.49 (1H, d, J=2.04 Hz), 7.5-7.54 (1H, d, J=3.6 Hz), 7.94-7.96 (1H, d, J=8.92 Hz).

EXAMPLE 22

1-[(3-(1-Methylpiperidin-4-yl)amino)-4-methoxy]benzenesulfonyl-5-fluoroindole

Using a similar procedure as given in the preparation of EXAMPLE 1 and some non-critical variations above derivative was prepared. IR spectra (Cm$^{-1}$): 1147, 1167, 1518, 2942, 3395; Mass (m/z): 418.5 (M+H)$^+$, $^1$H-NMR (δ, ppm): 1.37-1.47 (2H, m), 1.86-1.9 (2H, m), 2.09-2.14 (2H, m), 2.32 (3H, s), 2.77-2.8 (2H, d, J=11.4 Hz), 3.15-3.17 (1H, m), 3.82 (3H, s), 4.23-4.25 (1H, d, J=7.84 Hz), 6.57-6.58 (1H, d, J=3.56 Hz), 6.67-6.69 (1H, d, J=8.48 Hz), 6.82-6.82 (1H, d, J=2.28 Hz), 6.99-7.05 (1H, m), 7.15-7.19 (2H, m), 7.56-7.56 (1H, d, J=3.6 Hz), 7.94-7.96 (1H, m).

EXAMPLE 23

1-[(3-(1-Methylpiperidin-4-yl)amino)-4-methoxy]benzenesulfonyl-4-chloroindole Using a similar procedure as given in the preparation of EXAMPLE 1 and some non-critical variations above derivative was prepared. IR spectra (Cm$^{-1}$): 1132, 1162, 1519, 2936, 3421; Mass (m/z): 434.3 (M+H)$^+$, 436.3 (M+2)$^+$; $^1$H-NMR (δ, ppm): 1.37-1.47 (2H, m), 1.87-1.91 (2H, m), 2.09-2.17 (2H, m), 2.32 (3H, s), 2.77-2.8 (2H, d,), 3.13-3.2 (1H, m), 3.82 (3H, s), 4.24-4.26 (1H, d, J=7.84 Hz), 6.67-6.69 (1H, d, J=8.44 Hz), 6.74-6.75 (1H, d, J=3.92 Hz), 6.83-6.84 (1H, d, J=2.28 Hz), 7.18-7.22 (3H, m), 7.58-7.59 (1H, d, J=3.76 Hz), 7.9-7.94 (1H, m).

EXAMPLE 24

1-[(3-(1-Methylpiperidin-4-yl)amino)-4-methoxy]benzenesulfonyl-6-chloroindole Using a similar procedure as given in the preparation of EXAMPLE 1 and some non-critical variations above derivative was prepared. IR spectra (Cm$^{-1}$): 1135, 1268, 1520, 2937, 3423; Mass (m/z): 434.5, 436.5 (M+H)$^+$; $^1$H-NMR (δ, ppm): 1.4-1.49 (2H, m), 1.91-1.95 (2H, m), 2.14-2.19 (2H, m), 2.32 (3H, s), 2.78-2.81 (2H, d, J=11.2 Hz), 3.17-3.21 (1H, m), 3.83 (3H, s), 4.25-4.27 (1H, d, J=7.72 Hz), 6.58-6.59 (1H, d, J=3.56 Hz), 6.66-6.71 (1H, d, J=8.52 Hz), 6.9-6.9 (1H, d, J=2.28 Hz), 7.17-7.2 (2H, m), 7.41-7.43 (1H, d, J=8.36 Hz), 7.51-7.52 (1H, d, J=3.64 Hz), 8.05-8.06 (1H, d, J=1.56 Hz).

EXAMPLE 25

1-[3-(1-Methylpiperidin-4-yl)amino-4-Fluoro]benzenesulfonylindole

Using a similar procedure as given in the preparation of EXAMPLE 1 and some non-critical variations above derivative was prepared. IR spectra (Cm$^{-1}$): 1130, 1375, 1522, 2939, 3404; Mass (m/z): 388.3 (M+H)$^+$; $^1$H-NMR (δ, ppm): 1.4-1.47 (2H, m), 1.85-1.9 (2H, m), 2.1-2.15 (2H, m), 2.32 (3H, s), 2.77-2.79 (2H, m), 3.13-3.22 (1H, m), 3.92-3.95 (1H, m), 6.65-6.66 (1H, m), 6.92-6.94 (1H, d, J=8.4), 6.95-6.97 (1H, d, 8.44), 7.0-7.3 (1H, dd, J=2.28 and 7.74 Hz), 7.09-7.13 (1H, m), 7.21-7.5 (1H, td), 7.27-7.33 (1H, td, J=0.64 and 7.36), 7.5-7.51 (1H, d, J=3.68), 7.52-7.55 (1H, d, 9.6), 7.99-8.22 (1H, dd, J=0.6 and 7.36).

EXAMPLE 26

1-[3-(1-Methylpiperidin-4-yl)amino]benzenesulfonyl-3-bromoindole

1-[3-(1-Methylpiperidin-4-yl)amino]benzenesulfonylindole was subjected to bromination using the literature methods to obtain this derivative. Mass (m/z): 449 (M+H)$^+$, 451 (M+H)$^+$.

EXAMPLE 27

1-[3-(1-Methylpiperidin-4-yl)amino-4-methoxy]benzenesulfonyl-3-bromoindole

1-[3-(1-Methylpiperidin-4-yl)amino-4-methoxy]benzenesulfonylindole was subjected to bromination using the literature methods to obtain this derivative. Mass (m/z): 479 (M+H)$^+$, 481 (M+H)$^+$.

EXAMPLE 28

1-[3-(1-Methylpiperidin-4-yl)amino]benzenesulfonyl-3-bromo-5-fluoroindole

1-[3-(1-Methylpiperidin-4-yl)amino]benzenesulfonyl-5-fluoroindole was subjected to bromination using the literature methods to obtain this derivative. Mass (m/z): 467 (M+H)$^+$, 469 (M+H)$^+$.

EXAMPLE 29

1-[3-(1-Methylpiperidin-4-yl)amino]benzenesulfonyl-3-bromo-4-chloroindole

1-[3-(1-Methylpiperidin-4-yl)amino]benzenesulfonyl-4-chloroindole was subjected to bromination using the literature methods to obtain this derivative. Mass (m/z): 484 (M+H)$^+$, 486 (M+H)$^+$.

EXAMPLE 30

1-[3-(1-Methylpiperidin-4-yl)methylamino]benzenesulfonylindole

Using a similar procedure as given in the preparation of EXAMPLE 1 and using the modified starting material, 1-[3-methylamino]benzenesulfonylindole, and some non-critical variations above derivative was prepared. Mass (m/z): 384 (M+H)$^+$.

EXAMPLE 31

1-[3-(1-Methylpiperidin-4-yl)methylamino]benzenesulfony-5-methoxy-indole

Using a similar procedure as given in the preparation of EXAMPLE 1 and using the modified starting material, 1-[3-methylamino]benzenesulfonyl-5-methoxyindole, and some non-critical variations above derivative was prepared. Mass (m/z): 414 (M+H)$^+$.

EXAMPLE 32

1-[3-(1-Methylpiperidin-4-yl)methylamino]benzenesulfony-5-fluoroindole

Using a similar procedure as given in the preparation of EXAMPLE 1 and using the modified starting material, 1-[3-methylamino]benzenesulfonyl-5-fluoroindole, and some non-critical variations above derivative was prepared. Mass (m/z): 402 (M+H)$^+$.

EXAMPLE 33

1-[3-(1-Methylpiperidin-4-yl)acetamido]benzene-sulfony-5-fluoroindole

1-[3-(1-Methylpiperidin-4-yl)amino]benzenesulfony-5-fluoroindole was acetylated using the acetyl chloride and dichloromethane using the existing literature methods. Mass (m/z): 430 (M+H)$^+$

EXAMPLE 34

1-[3-(1-Methylpiperidin-4-yl)acetamido]benzene-sulfonyindole

1-[3-(1-Methylpiperidin-4-yl)amino]benzenesulfonyindole was subjected to reductive acylation with acetyl chloride using the procedure of example 33 and the same was in-situ subjected to reduction using sodium borohydride in acetic acid. Mass (m/z): 412 (M+H)$^+$.

EXAMPLE 35

1-[3-(1-Methylpiperidin-4-yl)ethylamino]benzene-sulfony-5-fluoroindole

Using a similar procedure as given in the preparation of EXAMPLE 34 and some non-critical variations above derivative was prepared. Mass (m/z): 416 (M+H)$^+$.

EXAMPLE 36

1-[3-(1-Methylpiperidin-4-yl)amino]benzenesulfonyl-5-fluoro indole Hydrochloride salt 1-[3-(1-Methylpiperidin-4-yl)amino]benzenesulfonyl-5-fluoroindole (EXAMPLE 6, 100 mg) was dissolved in minimum amount of IPA and the solution was cooled. The saturated solution of Hydrochloric acid (13.5%) in IPA was added slowly to this cooled solution and was allowed to stir. The white crystalline salt separated, which was filtered and washed with cold IPA.

EXAMPLE 37

1-[3-(1-Methylpiperidin-4-yl)amino-4-methoxy] benzenesulfonyl-1H-indole Hydrochloride salt Using a similar procedure as given in the preparation of EXAMPLE 36, this salt of example 17 was prepared.

EXAMPLE 38

Food Intake Measurement (Behavioural Model)

Male Wistar rats (120-140 g) obtained from N.I.N. (National Institute of Nutrition, Hyderabad, India) were used. The chronic effect of the compounds of general formula (I) on food intake in well-fed rats was then determined as follows.

The rats were housed in their single home cages for 28 days. During this period, the rats were either dosed orally or i.p., with a composition comprising a compound of formula (I) of a corresponding composition (vehicle) without the said compound (control group), once-a-day. The rat is provided with ad libitum food and water.

On 0, 1$^{st}$, 7$^{th}$, 14$^{th}$, 21$^{st}$ and 28$^{th}$ day the rat is left with the pre-weighed amounts of food. Food intake and weight gain is measured on the routine basis. Also a food ingestion method is disclosed in the literature (Kask et al., European Journal of Pharmacology, 414, 2001, 215-224, and Turnball et. Al., Diabetes, vol 51, August, 2002, and some in-house modifications.). The respective parts of the descriptions are herein incorporated as a reference, and they form part of the disclosure.

Some representative compounds have shown the statistically significant decrease in food intake, when conducted in the above manner at the doses of either 10 mg/Kg, or 30 mg/Kg or both.

EXAMPLE 39

Tablet Comprising a Compound of Formula (I)

| | |
|---|---|
| Compound according to example 1 | 5 mg |
| Lactose | 60 mg |
| Crystalline cellulose | 25 mg |
| K 90 Povidone | 5 mg |
| Pregelatinised starch | 3 mg |
| Colloidal silicon dioxide | 1 mg |
| Magnesium stearate | 1 mg |
| Total weight per tablet | 100 mg |

The ingredients are combined and granulated using a solvent such as methanol. The formulation is then dried and formed into tablets (containing about 20 mg of active compound) with an appropriate tablet machine.

EXAMPLE 40

Composition for Oral Administration

| Ingredient | % wt./wt. |
|---|---|
| Active ingredient | 20.0% |
| Lactose | 79.5% |
| Magnesium stearate | 0.5% |

The ingredients are mixed and dispensed into capsules containing about 100 mg each one capsule would approximate a total daily dosage.

EXAMPLE 41

Liquid Oral Formulation

| Ingredient | Amount |
|---|---|
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 g |
| Colorings | 0.5 g |
| Distilled water | q.s. to 100 ml |

The ingredients are mixed to form a suspension for oral administration.

EXAMPLE 42

Parenteral Formulation

| Ingredient | % wt./wt. |
|---|---|
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

EXAMPLE 43

Suppository Formulation

| Ingredient | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

EXAMPLE 44

Topical Formulation

| Ingredients | grams |
|---|---|
| Active compound | 0.2-2 g |
| Span 60 | 2 g |
| Tween 60 | 2 g |
| Mineral oil | 5 g |
| Petrolatum | 10 g |
| Methyl paraben | 0.15 g |
| Propyl paraben | 0.05 g |
| BHA (butylated hydroxy anisole) | 0.01 g |
| Water | 100 ml |

All of the ingredients, except water, are combined and heated to about 60° C. with stirring. A sufficient quantity of water at about 60° C. is then added with vigorous stirring to emulsify the ingredients, and water then added q.s. about 100 g.

EXAMPLE 45

Object Recognition Task Model

The cognition-enhancing properties of compounds of this invention were estimated using a model of animal cognition: the object recognition task model.

Male wistar rats (230-280 g) obtained from N I.N. (National Institute of Nutrition, Hyderabad, India) were used as an experimental animal. Four animals were housed in each cage. Animals were kept on 20% food deprivation before one day and given water ad libitum throughout the experiment, and maintained on a 12 h light/dark cycle. Also the rats were habituated to individual arenas for 1 hour in absence of any objects.

One group of 12 rats received vehicle (1 mL/Kg) orally and another set of animals received compound of the formula (I) either orally or i.p., before one hour of the familiar (T1) and choice trial (T2). The experiment was carried out in a 50×50×50 Cm open field made up of acrylic. In the familiarization phase, (T1), the rats were placed individually in the open field for 3 min., in which two identical objects (plastic bottles, 12.5 Cm height×5.5 Cm diameter) covered in yellow masking tape alone (a1 and a2) were positioned in two adjacent corners, 10 Cm. from the walls. After 24 hour of the (T1) trial for long-term memory test, the same rats were placed in the same arena as they were placed in T1 trial. Choice phase (T2) rats were allowed to explore the open field for 3 min. in presence of one familiar object (a3) and one novel object (b) (Amber color glass bottle, 12 Cm high and 5 Cm in diameter. Familiar objects presented similar textures, colors and sizes. During the T1 and T2 trial, exploration of each object (defined as sniffing, licking, chewing or having moving vibrissae whilst directing the nose towards the object at a distance of less than 1 Cm) were recorded separately by stopwatch. Sitting on an object was not regarded as exploratory activity, however, it was rarely observed. T1 is the total time spent exploring the familiar objects (a1+a2). T2 is the total time spent exploring the familiar object and novel object (a3+b).

The object recognition test was performed as described by Ennaceur, A., Delacour, J., 1988, *A new one-trial test for neurobiological studies of memory in rats—Behavioral data*, Behav. Brain Res., 31, 47-59.

Some representative compounds have shown positive effects indicating the increased novel object recognition viz; increased exploration time with novel object and higher discrimination index. The data for one of the compound, EXAMPLE 6 is represented in FIG. 1.

EXAMPLE 34

Chewing/Yawning/Stretching induction by $5HT_6R$ antagonists

Male Wistar rats weighing 200-250 g were used. Rats were given vehicle injections and placed in individual, transparent chambers for 1 h each day for 2 days before the test day, to habituate them to the observation chambers and testing procedure. On the test day, rats were placed in the observation chambers immediately after drug administration and observed continuously for yawning, stretching, and chewing behaviors from 60 to 90 min after drug or vehicle injections. 60 minutes prior to the drug administration Physostigmine, 0.1 mg/kg i.p. was administered to all the animals. Average number of yawns, stretches, and vacuous chewing movements during the 30 min observation period were recorded.

The representative examples like example 1, example 6 and example 17 demonstrated 40-60% increase in the stretching, yawning and chewing behaviors in comparison with the vehicle treated groups, at 1 mg/Kg, 3 mg/Kg, 10 mg/Kg and 30 mg/Kg.

REFERENCE

1. King M. V., Sleight A., J., Woolley M. L., and et. Al. Neuropharmacology, 2004, 47, 195-204.

2. Bentey J. C., Bourson A., Boess F. G., Pone K. C. F., Marsden C. A., Petit N., Sleight A. J., British Journal of Pharmacology, 1999, 126 (7), 1537-1542).

EXAMPLE 35

Water Maze

The water maze apparatus consisted of a circular pool (1.8 m diameter, 0.6 m high) constructed in black Perspex (TSE systems, Germany) filled with water (24±2° C.) and positioned underneath a wide-angled video camera to track animal. The 10 $Cm^2$ perspex platform, lying 1 Cm below the water surface, was placed in the centre of one of the four imaginary quadrants, which remained constant for all rats. The black Perspex used in the construction of the maze and platform offered no intramaze cues to guide escape behavior. By contrast, the training room offered several strong extramaze visual cues to aid the formation of the spatial map necessary for escape learning. An automated tracking system, [Videomot 2 (5.51), TSE systems, Germany] was employed. This program analyzes video images acquired via a digital camera and an image acquisition board that determined path length, swim speed and the number of entries and duration of swim time spent in each quadrant of the water maze.

REFERENCE

1. Yamada N., Hattoria A., Hayashi T., Nishikawa T., Fukuda H. et. Al., Pharmacology, Biochem. And Behaviour, 2004, 78, 787-791.
2. Linder M. D., Hodges D. B>, Hogan J. B., Corsa J. A., et al The Journal of Pharmacology and Experimental Therapeutics, 2003, 307 (2), 682-691.

EXAMPLE 35

Passive Avoidance Apparatus

Animals were trained in a single-trial, step through, light-dark passive avoidance paradigm. The training apparatus consisted of a chamber 300 mm in length, 260 mm wide, and 270 mm in height, constructed to established designs. The front and top were transparent, allowing the experimenter to observe the behavior of the animal inside the apparatus. The chamber was divided into two compartments, separated by a central shutter that contained a small opening 50 mm wide and 75 mm high set close to the front of the chamber. The smaller of the compartments measured 9 mm in width and contained a low-power (6V) illumination source. The larger compartment measured 210 mm in width and was not illuminated. The floor of this dark compartment consisted of a grid of 16 horizontal stainless-steel bars that were 5 mm in diameter and spaced 12.5 mm apart. A current generator supplied 0.75 mA to the grid floor, which was scrambled once every 0.5 s across the 16 bars. A resistance range of 40-60 microohms was calculated for a control group of rats and the apparatus was calibrated accordingly. An electronic circuit detecting the resistance of the animal ensured an accurate current delivery by automatic variation of the voltage with change in resistance.
Experimental Procedure This was carried out as described previously (Fox et al., 1995). Adult male Wistar rats weighing 200-230 g were used. Animals were brought to the laboratory 1 h before the experiment. On the day of training, animals were placed facing the rear of the light compartment of the apparatus. The timer was started once the animal has completely turned to face the front of the chamber. Latency to enter the dark chamber was recorded (usually <20 s), and having completely entered the dark compartment an inescapable foot shock of 0.75 mA for 3 s was administered to the animal. Animals were then returned to their home cages. Between each training session, both compartments of the chamber were cleaned to remove any confounding olfactory cues. Recall of this inhibitory stimulus was evaluated 24 h, 72 h and on 7 day post-training by returning the animal into the light chamber and recording their latency to enter the dark chamber, a criterion time of 300 s was employed.

Some of the compounds did show the significant increase in latency to reach the dark zone, at 10 mg/Kg oral dose. The representative data for the example 6 is shown in FIG. 2 in graphical form.

The data shown in FIG. 2 demonstrates that the compounds of the present invention improve the cognition and more specifically, the consolidation of memory, in the time induced disruption model.

REFERENCE

1. Callahan P. M., Ilch C. P., Rowe N. B., Tehim A., Abst. 776. 19. 2004, Society for neuroscience, 2004.
2. Fox G. B., Connell A. W. U., Murphy K. J., Regan C. M., Journal of Neurochemistry, 1995, 65, 6, 2796-2799.

EXAMPLE 46

Nova Screen Binding Assay for Human 5-$HT_6$ Receptor

Pharmacological data Compounds can be tested according to the following the procedures.
Materials and Methods:
Receptor source: Human recombinant expressed in HEK293 cells
Radioligand: [$^3$H]LSD (60-80 Ci/mmol)
Final ligand concentration—[1.5 nM]
Non-specific determinant: Methiothepin mesylate—[0.1 µM]
Reference compound: Methiothepin mesylate
Positive control: Methiothepin mesylate
Incubation conditions: Reactions were carried out in 50 mM TRIS-HCl (pH 7.4) containing 10 mM $MgCl_2$, 0.5 mM EDTA for 60 minutes at 37° C. The reaction was terminated by rapid vacuum filtration onto glass fiber filters. Radioactivity trapped onto the filters was determined and compared to control values in order to ascertain any interactions of test compound(s) with the cloned serotonin -5$HT_6$ binding site.

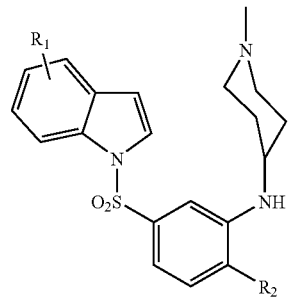

Radioligand binding data at 5$ht_6$R (h)

| Example No. | $R_1$ | $R_2$ | Ki | % Inhibition at 100 nM |
|---|---|---|---|---|
| 1 | —H | —H | 3.19 | 96.79 |
| 2 | 5-$OCH_3$ | —H | 12.50 | 82.23 |

-continued

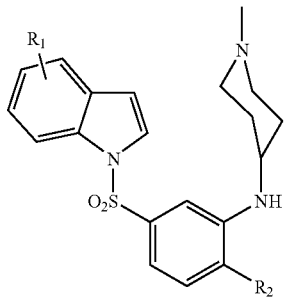

| Example No. | $R_1$ | $R_2$ | Radioligand binding data at 5ht$_6$R (h) | |
|---|---|---|---|---|
| | | | Ki | % Inhibition at 100 nM |
| 4 | 5-Br | —H | 10.30 | 92.17 |
| 6 | 5-F | —H | 7.00 | 93.23 |
| 10 | 5-OCH$_3$ | —CH$_3$ | 20.90 | 85.26 |
| 17 | —H | —OCH$_3$ | 1.29 | 101.05 |
| 25 | —H | —F | | 99.33 |

Literature Reference: Monsma F. J. Jr., et al., Molecular Cloning and Expression of Novel Serotonin Receptor with High Affinity for Tricyclic Psychotropic Drugs. Mol. Pharmacol. (43): 320-327 (1993).

EXAMPLE 47 cAMP Assay

The antagonist property of the compounds at the human 5-HT$_6$ receptors was determined by testing their effect on cAMP accumulation in stably transfected HEK293 cells. Binding of an agonist to the human 5-HT$_6$ receptor will lead to an increase in adenyl cyclase activity. A compound that is an agonist will show an increase in cAMP production and a compound that is an antagonist will block the agonist effect.

Human 5-HT$_6$ receptors were cloned and stably expressed in HEK293 cells. These cells were plated in 6 well plates in DMEM/F12 media with 10% fetal calf serum (FCS) and 500 ug/mL G418 and incubated at 37° C. in a CO$_2$ incubator. The cells were allowed to grow to about 70% confluence before initiation of the experiment. On the day of the experiment, the culture media was removed, and the cells were washed once with serum free medium (SFM).

Two mL of SFM+IBMX media was added and incubated at 37° C. for 10 min. The media were removed and fresh SFM+IBMX media containing various compounds, and 1 uM serotonin (as antagonist) were added to the appropriate wells and incubated for 30 min. Following incubation, the media were removed and the cells were washed once with 1 mL of PBS (phosphate buffered saline). Each well was treated with 1 mL cold 95% ethanol and 5 mM EDTA (2:1) at 4° C. for 1 hour. The cells were then scraped and transferred into Eppendorf tubes. The tubes were centrifuged for 5 min at 4° C., and the supernatants were stored at 4° C. until assayed.

cAMP content was determined by EIA (enzyme-immunoassay) using the Amersham Biotrak cAMP EIA kit (Amersham RPN 225). The procedure used is as described for the kit. Briefly, cAMP is determined by the competition between unlabeled cAMP and a fixed quantity of peroxidase-labelled cAMP for the binding sites on anti-cAMP antibody. The antibody is immobilized onto polystyrene microtitre wells precoated with a second antibody. The reaction is started by adding 50 uL, peroxidase-labeled-cAMP to the sample (100 uL) preincubated with the antiserum (100 uL) for 2 hours at 4° C. Following 1 hour incubation at 4° C., the unbound ligand is separated by a simple washing procedure. Then an enzyme substrate, trimethylbenzidine (1), is added and incubated at room temperature for 60 min. The reaction is stopped by the addition of 100 uL 1.0 M sulphuric acid and the resultant color read by a microtitre plate spectrophotometer at 450 nM within 30 minutes.

In the functional adenylyl cyclase assay, some of the compound of this invention was found to be a competitive antagonist with good selectivity over a number of other receptors including other serotonin receptors such as 5-HT$_{1A}$ and 5-HT$_7$.

We claim:
1. A compound having the Formula (I),

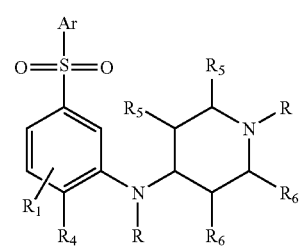

Formula (I)

wherein:
— Ar is an unsubstituted or substituted bicyclic heteroaryl, wherein substituents may be one or more and are independently selected from the group consisting of: hydrogen, halogen, (C$_1$-C$_3$)alkyl, halo(C$_1$-C$_3$)alkyl, (C$_1$-C$_3$) alkoxy, and halo(C$_1$-C$_3$)alkoxy;
R is selected from the group consisting of: (C$_1$-C$_3$)alkyl and halo(C$_1$-C$_3$)alkyl group;
at each occurrence, R$_1$ is independently selected from the group consisting of: hydrogen, halogen, (C$_1$-C$_3$)alkyl, halo(C$_1$-C$_3$)alkyl, and (C$_1$-C$_3$)alkoxy;
R$_4$ is hydrogen, halogen, (C$_1$-C$_3$)alkyl, halo(C$_1$-C$_3$)alkyl, (C$_1$-C$_3$)alkoxy, halo(C$_1$-C$_3$)alkoxy; and
at each occurrence, R$_5$ and R$_6$ is independently selected from the group consisting of: hydrogen, methyl, and a pharmaceutically acceptable salt thereof.

2. The compound as claimed in claim 1 wherein Ar is selected from the group consisting of: indolyl, indazolyl, pyrrolopyridinyl, benzofuranyl, benzothienyl and benzimidazolyl.

3. The compound as claimed in claim 1 wherein R is selected from the group consisting of: hydrogen and (C$_1$-C$_3$) alkyl.

4. The compound as claimed in claim 1 wherein R$_1$ is selected from the group consisting of: hydrogen, halogen, (C$_1$-C$_3$)alkyl, halo(C$_1$-C$_3$)alkyl, (C$_1$-C$_3$) alkoxy, and halo (C$_1$-C$_3$)alkoxy.

5. A compound as claimed in claim 1 wherein R$_5$ and R$_6$ represents hydrogen.

6. A compound as claimed in claim 1 selected from among the following group:
  1-[3-(1-Methylpiperidin-4-yl)amino]benzenesulfonyl-1H-indole;
  1-[3-(1-Methylpiperidin-4-yl)amino]benzenesulfonyl-5-methoxyindole;
  1-[3-(1-Methylpiperidin-4-yl)amino]benzenesulfonyl-5-isopropoxyindole;

1-[3-(1-Methylpiperidin-4-yl)amino]benzenesulfonyl-5-Bromoindole;
1-[3-(1-Methylpiperidin-4-yl)amino]benzenesulfonyl-5-chloroindole;
1-[3-(1-Methylpiperidin-4-yl)amino]benzenesulfonyl-5-fluoroindole;
1-[3-(1-Methylpiperidin-4-yl)amino]benzenesulfonyl-4-chloroindole;
1-[3-(1-Methylpiperidin-4-yl)amino]benzenesulfonyl-6-chloroindole;
1-[3-(1-Methylpiperidin-4-yl)amino-4-methyl]benzenesulfonylindole;
1-[3-(1-Methylpiperidin-4-yl)amino-4-methyl]benzenesulfonyl-5-methoxyindole;
1-[3-(1-Methylpiperidin-4-yl)amino-4-methyl]benzenesulfonyl-5-isopropoxyindole;
1-[3-(1-Methylpiperidin-4-yl)amino-4-methyl]benzenesulfonyl-5-bromoindole;
1-[3-(1-Methylpiperidin-4-yl)amino-4-methyl]benzenesulfonyl-5-chloroindole;
1-[3-(1-Methylpiperidin-4-yl)amino-4-methyl]benzenesulfonyl-5-fluoroindole;
1-[3-(1-Methylpiperidin-4-yl)amino-4-methyl]benzenesulfonyl-4-chloroindole;
1-[3-(1-Methylpiperidin-4-yl)amino-4-methyl]benzenesulfonyl-6-chloroindole;
1-[3-(1-Methylpiperidin-4-yl)amino-4-methoxy]benzenesulfonyl-1H-indole;
1-[(3-(1-Methylpiperidin-4-yl)amino)-4-methoxy]benzenesulfonyl-5-methoxyindole;
1-[(3-(1-Methylpiperidin-4-yl)amino)-4-methoxy]benzenesulfonyl-5-isopropoxyindole;
1-[(3-(1-Methylpiperidin-4-yl)amino)-4-methoxy]benzenesulfonyl-5-bromoindole;
1-[(3-(1-Methylpiperidin-4-yl)amino)-4-methoxy]benzenesulfonyl-5-chloroindole;
1-[(3-(1-Methylpiperidin-4-yl)amino)-4-methoxy]benzenesulfonyl-5-fluoroindole;
1-[(3-(1-Methylpiperidin-4-yl)amino)-4-methoxy]benzenesulfonyl-4-chloroindole;
1-[(3-(1-Methylpiperidin-4-yl)amino)-4-methoxy]benzenesulfonyl-6-chloroindole;
1-[3-(1-Methylpiperidin-4-yl)amino-4-Fluoro]benzenesulfonylindole;
1-[3-(1-Methylpiperidin-4-yl)amino]benzenesulfonyl-3-bromoindole;
1-[3-(1-Methylpiperidin-4-yl)amino-4-methoxy]benzenesulfonyl-3-bromoindole;
1-[3-(1-Methylpiperidin-4-yl)amino]benzenesulfonyl-3-bromo-5-fluoroindole;
1-[3-(1-Methylpiperidin-4-yl)amino]benzenesulfonyl-3-bromo-4-chloroindole;
1-[3-(1-Methylpiperidin-4-yl)methylamino]benzenesulfonylindole;
1-[3-(1-Methylpiperidin-4-yl)methylamino]benzenesulfony-5-methoxy-indole;
1-[3-(1-Methylpiperidin-4-yl)methylamino]benzenesulfony-5-fluoroindole;
1-[3-(1-Methylpiperidin-4-yl)acetamido]benzenesulfony-5-fluoroindole;
1-[3-(1-Methylpiperidin-4-yl)acetamido]benzenesulfonyindole;
1-[3-(1-Methylpiperidin-4-yl)ethylamino]benzenesulfony-5-fluoroindole;
1-[3-(1-Methylpiperidin-4-yl)amino]benzenesulfonyl-5-fluoroindole Hydrochloride salt; and a stereoisomer thereof; and a slt thereof.

7. The compound of formula (I) as defined in claim 1 for use as a medicament.

8. A process for preparation of a compound of the Formula (I):

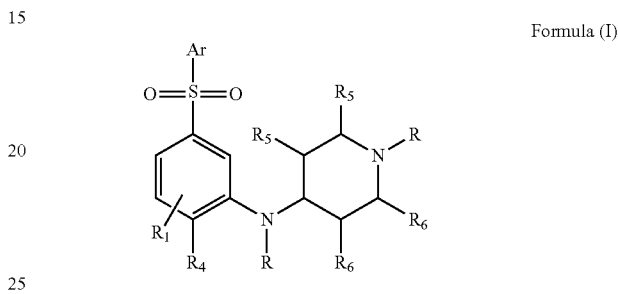

Formula (I)

the process comprising the steps of:
contacting a compound of the Formula (A):

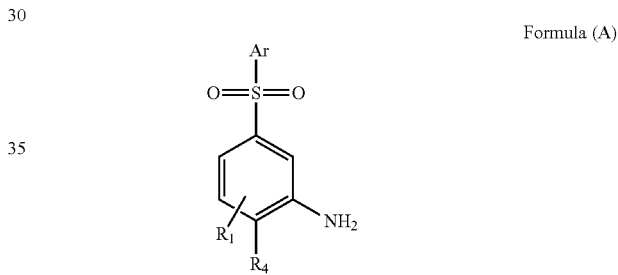

Formula (A)

with a piperidone of the Formula (B):

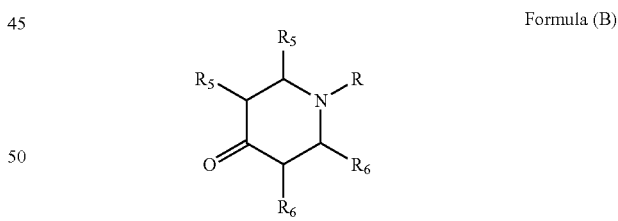

Formula (B)

by reductive amination using a suitable reducing agent/catalyst in the presence of inert solvent at ambient temperature to obtain a compound of the Formula (I), wherein all substitutions are as defined in claim 1.

* * * * *